US012610975B1

(12) United States Patent
Akiva et al.

(10) Patent No.: US 12,610,975 B1
(45) Date of Patent: Apr. 28, 2026

(54) FAMILY OF HEME BINDING PROTEINS THAT INCREASE CHELATED IRON CONTENT AND IMPROVE FLAVOR OF NUTRITIONAL SUPPLEMENTS AND FOOD PRODUCTS

(71) Applicant: Shiru, Inc., Berkeley, CA (US)

(72) Inventors: Eyal Akiva, Tel Aviv (IL); Christopher Farwell, Richmond, CA (US); Michael Madonna, Novato, CA (US); Michael Schiff, Menlo Park, CA (US); Jason Voogt, Lafayette, CA (US)

(73) Assignee: Shiru, Inc., Berkeley, CA (US)

( * ) Notice: Subject to any disclaimer, the term of this patent is extended or adjusted under 35 U.S.C. 154(b) by 0 days.

(21) Appl. No.: 18/144,827

(22) Filed: May 8, 2023

Related U.S. Application Data

(60) Provisional application No. 63/339,901, filed on May 9, 2022.

(51) Int. Cl.

| | |
|---|---|
| *A61K 38/44* | (2006.01) |
| *A21D 2/26* | (2006.01) |
| *A21D 13/80* | (2017.01) |
| *A23G 9/38* | (2006.01) |
| *A23G 9/42* | (2006.01) |
| *A23J 3/14* | (2006.01) |
| *A23J 3/22* | (2006.01) |
| *A23L 9/10* | (2016.01) |
| *A23L 23/00* | (2016.01) |
| *A23L 27/26* | (2016.01) |
| *A23L 33/00* | (2016.01) |
| *A23L 33/115* | (2016.01) |
| *A23L 33/185* | (2016.01) |
| *A61K 38/41* | (2006.01) |

(52) U.S. Cl.
CPC ............ *A23L 33/185* (2016.08); *A21D 2/264* (2013.01); *A21D 13/80* (2017.01); *A23G 9/38* (2013.01); *A23G 9/42* (2013.01); *A23J 3/14* (2013.01); *A23J 3/227* (2013.01); *A23L 9/10* (2016.08); *A23L 23/00* (2016.08); *A23L 27/26* (2016.08); *A23L 33/115* (2016.08); *A23L*
*33/40* (2016.08); *A61K 38/41* (2013.01); *A61K 38/44* (2013.01); *C12Y 111/01019* (2013.01)

(58) Field of Classification Search
CPC .......... A23L 33/185; A23L 9/10; A23L 23/00; A23L 27/26; A23L 33/115; A23L 33/40; A21D 2/264; A21D 13/80; A23G 9/39; A23G 9/42; A23J 3/14; A23J 3/227; A61K 38/41; A61K 38/44
See application file for complete search history.

(56) References Cited

FOREIGN PATENT DOCUMENTS

CN       102265917 A   * 12/2011

OTHER PUBLICATIONS

Zou et al. The Genome of Broomcorn Millet, Nat. Communications, 2019; 10:436, pp. 1-11.*
Bhat et al. Environment Conservation Journal, 20 (3): 113-124, 2019.*

* cited by examiner

*Primary Examiner* — Jeanette M Lieb
(74) *Attorney, Agent, or Firm* — MS IP Law

(57) ABSTRACT

This disclosure provides materials and methods for improving the nutritional value of food products by increasing the content of chelated iron. Heme binding proteins (designated as PX90 proteins) that have not previously been used as food additives are manufactured by recombinant expression, and then included in food products during manufacture or preparation. PX90 proteins may also impart a meat-like flavor or aroma, either coincidentally or by design. Subcategories of PX90 proteins are structurally related to THAP4-like hemebinding beta-barrel domain containing proteins, indoleamine 2,3-dioxygenase (IDO), DyP-type peroxidase, ferritins, and hemopexins. The bioavailable iron in nutritional supplements and food products of this disclosure is especially beneficial for consumers who have manifestations of iron deficiency, low blood hematocrit, anemia, and other hematological abnormalities.

10 Claims, 18 Drawing Sheets

Specification includes a Sequence Listing.

A     AruPrx1c (HRP pdb:1ATJ)

B     BtLPO (pdb:3BXI)

C     BadDyP (pdb: 3AFV)

D     AaeAPO (pdb: 2YOR)

FIG. 3F                                    FIG. 3G
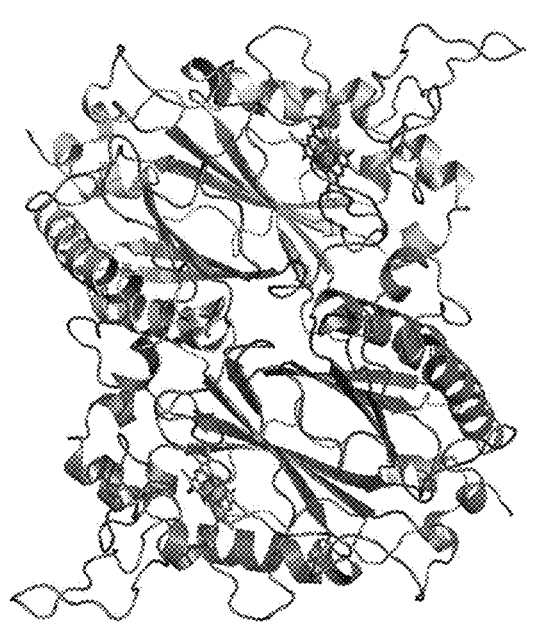
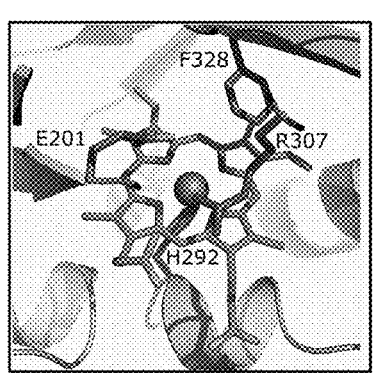
FIG. 4A                                    FIG. 4B
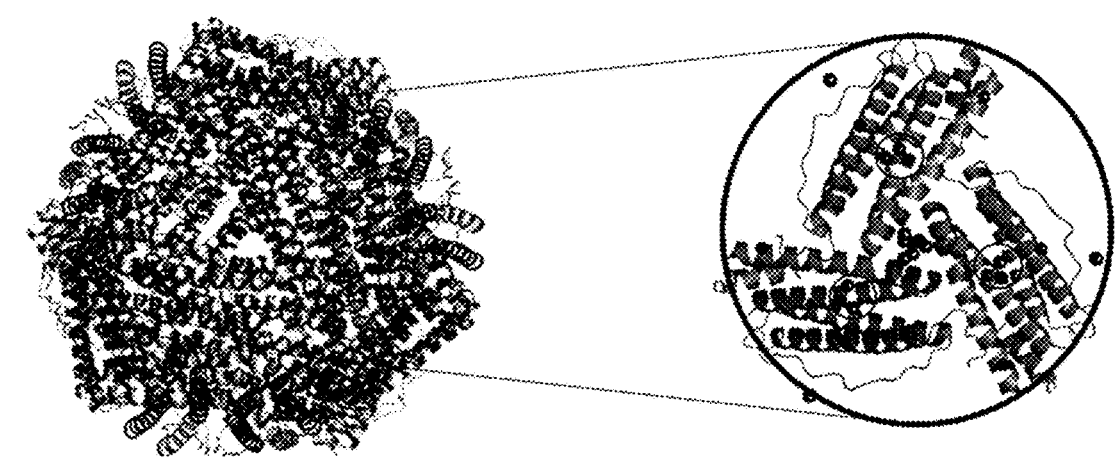

FIG. 4C
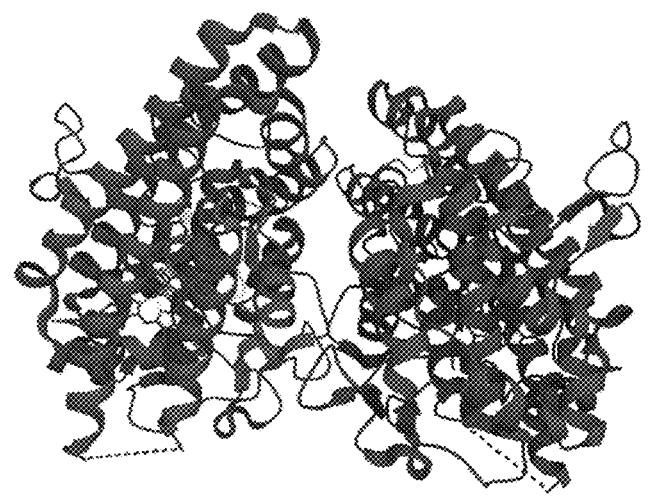
FIG. 4D
FIG. 4E
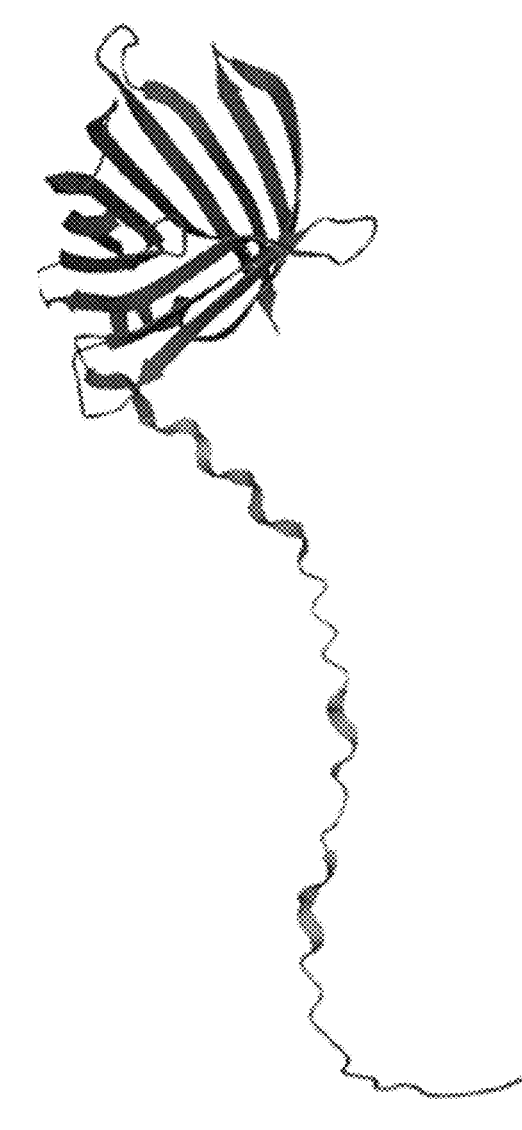

FIG. 6

*Amino acid sequences of proteins listed in TABLE 2*

SEQ. ID NO:1

```
DEFINITION  Full=Albumin-2; AltName: Full=24 kDa albumin; Short=LS-24;
            AltName: Full=PA2.
ACCESSION   D4AEP7
VERSION     D4AEP7.2

1 TKPGYINAAF RSSKNNEAYF FINDKYVLLD YAPGSSRDKV LYGPTPVRDG FKSLNQTIFG
        61 SYGIDCSFDT ENNEAFIFYE NFCALIDYAP HSKKDKIILG PKKIADVFPF FEGTVFESGI
       121 DAAYRSTRGK EVYLFKGDQY ARIDYGSNSM VNKEIKSISS GYPCFRNTIF ESGADAAFAS
       181 HKTNEVYFFK DDHYARVKVT PGGKLAIMDG VREIVDYWPS LKDIVPL

AUTHORS     Gaur,V., Qureshi,I.A., Singh,A., Chanana,V. and Salunke,D.M.
TITLE       Crystal structure and functional insights of hemopexin fold
protein
            from grass pea
JOURNAL     Plant Physiol 152 (4), 1842-1850 (2010)
```

SEQ ID NO:2

```
DEFINITION  Chain A, hemopexin fold protein CP4.
ACCESSION   3OYO_A
SOURCE      Vigna unguiculata (cowpea)

1 APYINAAFRS SSEYEVYFFA KNKYVRLHYT PGASSDTILT NLRLISSGFP SLAGTPFAEP
        61 GIDCSFHTEA SEAYVFSGNH SAYIDYAPGT TNDKILVGPT TIAEMFPVLN NTVFEDSIDS
       121 AFRSTKGKEV YLFKGNKYVR IAYDSKQLVG NIRNIGDGFP VLNGTEFESG IDACFASHKE
       181 PEAYLFKGQN YVRIDFTPGG KADTLVGNIR PILDGWPVLK GIFPV
```

Gaur,V., Chanana,V., Jain,A. and Salunke,D.M. Acta Crystallogr. Sect. F
Struct. Biol. Cryst. Commun. 67 (PT 2) 193-200 (2011)

SEQ ID NO:3

```
DEFINITION  major seed albumin [Pisum sativum].
ACCESSION   AAA33641
VERSION     AAA33641.1
SOURCE      Pisum sativum (pea)

1 MTKTGYINAA FRSSQNNEAY LFINDKYVLL DYAPGTSNDK VLYGPTPVRD GFKSLNQTVF
        61 GSYGVDCSFD TDNDEAFIFY EKFCALIDYA PHSNKDKIIL GPKKIADMFP FFEGTVFENG
       121 IDAAYRSTRG KEVYLFKGDQ YARIDYETNS MVNKEIKSIR NGFPCFRNTI FESGTDAAFA
       181 SHKTNEVYFF KGDYYARVTV TPGATDDQIM DGVRKTLDYW PSLRGIIPLE N

AUTHORS     Higgins,T.J., Beach,L.R., Spencer,D., Chandler,P.M.,
Randall,P.J.,
            Blagrove,R.J., Kortt,A.A. and Guthrie,R.E.
TITLE       cDNA and protein sequence of a major pea seed albumin (PA 2 : Mr
            approximately 26 000)
JOURNAL     Plant Mol. Biol. 8 (1), 37-45 (1987)
```

FIG. 6 continued

SEQ ID NO:4

```
DEFINITION  mung bean seed albumin [Vigna radiata var. radiata].
ACCESSION   CAA50008
VERSION     CAA50008.1
SOURCE      Vigna radiata var. radiata (mung bean)
/gene="MBSA"

1 MSNLPYINAA FRFSSRDYEV YFFAKNKYVR LQYTPGKTED KILTNLRLIS SGFPSLAGTP
       61 FAEPGIDSAF HTEASEAYVF SANNRAYIDY APGTTNDKIL AGPTTIAEMF PVLRNTVFAD
      121 SIDSAFRSTK GKEVYLFKGN KYVRIDYDSK QLVGSIRNIS DGFPVLNGTG FESGIDASFA
      181 SHKEPEAYLF KGDKYVRIHF TPGKTDDTLV GDVRPILDGW PVLKAFCLCE LNKPSLSCIN
      241 HLSLVTINKA FISNVCLFFF NVTLGLEACF LS

AUTHORS     Liu,F., Wilson,K.A. and Tan-Wilson,A.
TITLE       Cloning of a seed albumin cDNA (Accession No. X70671) from the
mung
            bean (Vigna radiata (L.) Wilczek)
JOURNAL     Plant Mol. Biol. In press
```

SEQ ID NO:5

```
DEFINITION  Hemopexin [Medicago truncatula].
ACCESSION   ABE87586
VERSION     ABE87586.1
SOURCE      Medicago truncatula (barrel medic)

1 MYRWSRKPYQ EIFTNGFQAP DQGNADNNIY HDLDGFVHSV GVPVDPNRAV PRAFISTTIN
       61 NAWRPNPSTD VLPIGSQIQL YRYEIFAPGG IWSAVTLKGR YQNPNLAEIT FVAGIAPQYI
      121 CSVQMYTATR PRGDGFPTMT REIKLIMNSH FLPHMDLHFT IYTPLTYYKD DNGMRRELPK
      181 ETYTPHESKV HKREVSSSQD NEEVGLHSYG AVEATPIYIN AAFRASANNE AYLFMNDECV
      241 LINYGRGSTN DHIVNGPLYI YDGYPSLSRT PFGEHGIDCA FDTDKTQAYI FSANLCALID
      301 YAPRTTDDKI VSGPMTITDM FPFFKDTVFE RGLDAAFRAH SSNEAYLFRG GHYALINYSS
      361 KKLIHIETIR HGFHSLIGTV FENGVEAAFA SHATKEAYLF KGEYYANIYY APGTTDDYLI
      421 GGRVKPILSN WPSLSSILPR DNGRLDLRSH KDHTDEDYGP VEL

AUTHORS     Lin,S., Dixon,R., May,G., Sumner,L., Gonzales,B., Cook,D.,
Kim,D.,
            Young,N., Cannon,S. and Roe,B.A. (direct submission)
```

SEQ ID NO:6

```
DEFINITION  histidine-rich protein [Oryza sativa Japonica Group].
ACCESSION   BAD06580
VERSION     BAD06580.1
SOURCE      Oryza sativa Japonica Group (Japanese rice)

1 MARHAVAAVL LLVALSPIVH GEADQEAVPA YVEYSGGDAA GTPVAIVPPY LDGAAARDEP
       61 AAAKSYLPAV AASPEGPVIP VYDDAADQHG FLRFPCRYRH HMRHGGFYRH RHGHEGFHGK
      121 EEKQKLVFEM PVEPATRGEE RREEEEGVVL PVAEPVPDSR RQDAAVAAAE EEDEDEMARL
      181 HHGRRSHHHH HRHHHHHHDE HEEDDHEQAD EASPAVERLI SFHHRRHHHH EEDNHEQREE
      241 GAPMKRFRRQ HHHYEEESEM RTKRFHQHHH KDDDERELEE MARRWIRKAL MSSRMHHHRG
      301 CRFHHHHHHL SFRHRAEDAA AAGEEEEKGG VMSWLKDFVN RF

AUTHORS     Sharma,A. and Komatsu,S. (direct submission)
TITLE       OsHRP
```

FIG. 6 continued

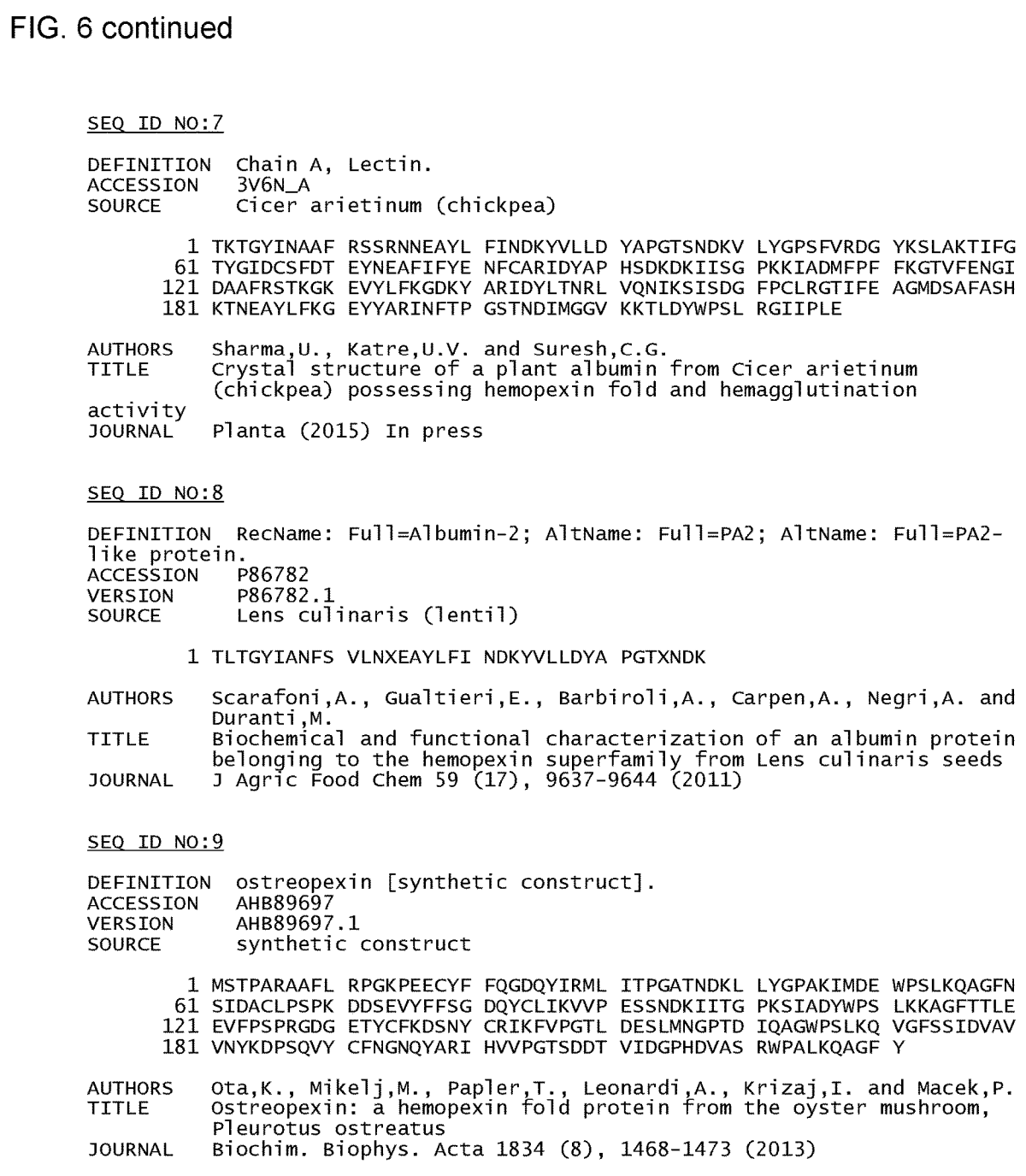

SEQ ID NO:7

```
DEFINITION  Chain A, Lectin.
ACCESSION   3V6N_A
SOURCE      Cicer arietinum (chickpea)

1  TKTGYINAAF RSSRNNEAYL FINDKYVLLD YAPGTSNDKV LYGPSFVRDG YKSLAKTIFG
        61  TYGIDCSFDT EYNEAFIFYE NFCARIDYAP HSDKDKIISG PKKIADMFPF FKGTVFENGI
       121  DAAFRSTKGK EVYLFKGDKY ARIDYLTNRL VQNIKSISDG FPCLRGTIFE AGMDSAFASH
       181  KTNEAYLFKG EYYARINFTP GSTNDIMGGV KKTLDYWPSL RGIIPLE

AUTHORS     Sharma,U., Katre,U.V. and Suresh,C.G.
TITLE       Crystal structure of a plant albumin from Cicer arietinum
            (chickpea) possessing hemopexin fold and hemagglutination
activity
JOURNAL     Planta (2015) In press
```

SEQ ID NO:8

```
DEFINITION  RecName: Full=Albumin-2; AltName: Full=PA2; AltName: Full=PA2-
like protein.
ACCESSION   P86782
VERSION     P86782.1
SOURCE      Lens culinaris (lentil)

1  TLTGYIANFS VLNXEAYLFI NDKYVLLDYA PGTXNDK

AUTHORS     Scarafoni,A., Gualtieri,E., Barbiroli,A., Carpen,A., Negri,A. and
            Duranti,M.
TITLE       Biochemical and functional characterization of an albumin protein
            belonging to the hemopexin superfamily from Lens culinaris seeds
JOURNAL     J Agric Food Chem 59 (17), 9637-9644 (2011)
```

SEQ ID NO:9

```
DEFINITION  ostreopexin [synthetic construct].
ACCESSION   AHB89697
VERSION     AHB89697.1
SOURCE      synthetic construct 1  MSTPARAAFL RPGKPEECYF FQGDQYIRML ITPGATNDKL LYGPAKIMDE WPSLKQAGFN
        61  SIDACLPSPK DDSEVYFFSG DQYCLIKVVP ESSNDKIITG PKSIADYWPS LKKAGFTTLE
       121  EVFPSPRGDG ETYCFKDSNY CRIKFVPGTL DESLMNGPTD IQAGWPSLKQ VGFSSIDVAV
       181  VNYKDPSQVY CFNGNQYARI HVVPGTSDDT VIDGPHDVAS RWPALKQAGF Y AUTHORS     Ota,K., Mikelj,M., Papler,T., Leonardi,A., Krizaj,I. and Macek,P.
TITLE       Ostreopexin: a hemopexin fold protein from the oyster mushroom,
            Pleurotus ostreatus
JOURNAL     Biochim. Biophys. Acta 1834 (8), 1468-1473 (2013)
```

FIG. 6 continued

SEQ ID NO:10

```
DEFINITION   Chain A, 2S Albumin protein.
ACCESSION    6IX1_A
SOURCE       Dolichos 1 ASYINAAFRS SRAYEVYFFE CNKYVRVYYT PGKTDDKILT NLRLISSGFP SLAGTAFAEP
       61 GIDCSFDTEA SEAYVFSGSQ CAYIDYAPGT TNDKILSGPT TIAEMFPVLK NTVFEDGIDS
      121 AFRSTKGKEV YLFKGNKYGR IAYDSKQLVG TIRNITDGFP VLKGTIFESG IDASFASHKE
      181 PEAYLFKGAQ YVRIKFTPGA TNNTLTGKVR PILDGWPCLR DILPT AUTHORS   Sharma,S.C., Kumar,A., Vashisht,S. and Salunke,D.M.
TITLE     High resolution structural and functional analysis of a hemopexin
          motif protein from Dolichos
JOURNAL   Sci Rep 9 (1), 19828 (2019)
```

FIG. 7A

*Amino acid sequences of proteins listed in TABLE 1A*

SEQ ID NO:11

MNQLQQLQNPGESPPVHPFVAPLSYLLGTWRGQGEGEYPTIPSFRYGEEIRFSHSGKPVIAYTQKTWKLE
SGAPMHAESGYFRPRPDGSIEVVIAQSTGLVEVQKGTYNVDEQSIKLKSDLVGNASKVKEISREFELVDG
KLSYVVRMSTTTNPLQPHLKAILDKL

SEQ ID NO:12

MKNNKPSISFSFISLFLLVSAVAVSAINDEEPVKDTNGNPLKIETRYFIQPASDNNGGGLVPANVDLSHL
CPLGIVRTSLPYQPGLPVTISTPSSSEGNDVLTNTNIAITFDAPIWLCPSSKTWTVDSSSEEKYIITGGD
PKSGESFFRIEKYGNGKNTYKLVRYDNGEGKSVGSTKSLWGPALVLNDDDDSDENAFPIKFREVDTSKGS
VFKKSSLRMFPFV

SEQ ID NO:13

MRSSSLAWALGLVALANAQGSPTQWYDSITGVTFSRFYQQDTDASWGYIFPSASGGQAPDEFIGLFQGPA
SAGWIGNSLGGSMRNNPLLVGWVDGSTPRISARWATDYAPPSIYSGPRLTILGSSGTNGNIQRIVYRCQN
CTRWTGGAGGIPTTGSAVFGWAFHSTTKPLTPSDPSSGLYRHSHAAQYGFDIGNARTTLYDYYLQQLTNA
PPLSGGAPTQPPTQQPPTTTAPPPPPPSSTFVSCPGAPQPRYQMNVANGFRVAPVLGGLTMPRGITLDTR
GNLLVVERGRGLTGHTLDANGCVTSSKVVIQDTQINHGIDVHPSGRRIIASSGDIAWSWDYDPATMTATN
RRTLVTGMNNFYHFTRTVHISRKYPNLFALNVGSDGNIDVPTRQQNSGRAQIRVFDYDQLPQNGVPFVSQ
YGRVLGYGLRNDVGITEDRAGNIHSIENSLDNAYRMVNGQRRDIHTNNPAEKVYNLGDPSNPRAIFGGYP
DCYTVWEPSDFTDSPKQPGDWFTQDNSGQYTDAWCNANAVKPTLLLPPHTAPLDMKFGLGNDTNLYVALH
GSWNRQPPQGYKVVVVPGQYSASGEWSPTAPLAQSRTAWSDLLTNRNENQCSGFGNANCFRPVGLVWSAD
GQNLYVSSDTSGEVFIIKRMSGPIVQPPITQPPITTSPPTPTTPPVVQPPTTVAPPQASQTLWGQCGGQG
WTGPTLCPANSVCRESNQWYSQCVPA

SEQ ID NO:14

MKSLSFSLALGFGSTLVYSAPSPSSGWQAPGPNDVRAPCPMLNTLANHGFLPHDGKGITVNKTIDALGSA
LNIDANLSTLLFGFAATTNPQPNATFFDLDHLSRHNILEHDASLSRQDSYFGPADVFNEAVFNQTKSFWT
GDIIDVQMAANARIVRLLTSNLTNPEYSLSDLGSAFSIGESAAYIGILGDKKSATVPKSWVEYLFENERL
PYELGFKRPNDPFTTDDLGDLSTQIINAQHFPQSPGKVEKRGDTRCPYGYH

SEQ ID NO:15

MKYFPLFPTLVFAARVVAFPAYASLAGLSQQELDAIIPTLEAREPGLPPGPLENSSAKLVNDEAHPWKPL
RPGDIRGPCPGLNTLASHGYLPRNGVATPVQIINAVQEGLNFDNQAAVFATYAAHLVDGNLITDLLSIGR
KTRLTGPDPPPPASVGGLNEHGTFEGDASMTRGDAFFGNNHDFNETLFEQLVDYSNRFGGGKYNLTVAGE
LRFKRIQDSIATNPNFSFVDFRFFTAYGETTFPANLFVDGRRDDGQLDMDAARSFFQFSRMPDDFFRAPS
PRSGTGVEVVIQAHPMQPGRNVGKINSYTVDPTSSDFSTPCLMYEKFVNITVKSLYPNPTVQLRKALNTN
LDFFFQGVAAGCTQVFPYGRD

FIG. 7A continued

SEQ ID NO:16

MDPYKYRPSSSFNAPMWSTNSGAPVWNNDNSLTVGSRGPILLEDYHLVEKIADFDRERIPERVVHARGAT
AKGFFEVTHDVSHLTCADFLRAPGVQTPVIVRFSTVIHERGSPETLRDPRGFAIKFYTREGNWDLVGNNF
PVFFIRDGMKFPDMVHALKPNPKTHIQENWRILDFFSHHPESLHMFTFLFDDIGVPADYRHMDGSGVNTY
TLVNRAGKAHYVKFHWKPTCGVKSLLEEEAVTVGGTNHSHATKDLTDSIAAGNYPEWTFYIQTIDPDYEE
RFDFDPLDVTKTWPEDVVPLQPVGRLVLNRNIDNFFSENEQLAFCPGIIVPGVYYSDDKLLQTRIFSYSD
TQRHRLGPNYLLLPANAPKCSHHNNHYDGLMNFMHRDEEVDYFPSRFDPAKHAPRYPIPSRTLNGRREKM
VIEKENNFKQPGERYRSMDPARQERFINRWIDALSDPRLTHEIKAIWLSYWSQADKSLGQKLASRLSSKP
SM

SEQ ID NO:17

MSRPVKLFFLAFLALLAAVHGDLQIGFYNQSCPSAESLVQQAVAAAFANNSGIAPGLIRMHFHDCFVRGC
DASVLLDSTANNTAEKDAAPNNPSLRGFEVIAAAKSAVEAACPKTVSCADILAFAARDSAALAGNITYQV
PSGRRDGNVSLASEALTNIPAPTFNATQLINSFAGKNLTADEMVTLSGAHSIGVSHCFSFLNRIYNFSNT
SQVDPTLSSSYADLLRTKCPSNSTRFTPITVSLDIITPTVLDNRYYTGVQLTLGLLTSDQALVTEANLSA
AVKNNADNLTAWVAKFAQAIVKMGQIQVLTGTQGEIRTNCSVVNSASLGDIVMASGHLTEVATS

SEQ ID NO:18

MALSSSKFSSFSGFSLSPVSGNGVQKPCFCDLRVGEKWGSRKFRVSATTAPLTGVIFEPFEEVKKDYLAV
PSVPLVSLARQNFADECESVINEQINVEYNASYVYHSLFAYFDRDNVALKGFAKFFKESSEEHREHAEKL
MKYQNTRGGRVVLHPIKDVPSEFEHVEKGDALYAMELALSLEKLTNEKLLNVHSVAERNNDLEMTHFIEG
EYLAEQVEAIKKISEYVAQLRRVGKGHGVWHFDQRLLHGVHGA

SEQ ID NO:19

MKGKPAVLAQLHKLLRGELAARDQYFIHSRMYQDWGLEKLYSRIDHEMQDETAHASLLIERILFLEETPD
LSQQDPIRVGKTVPEMLQYDLDYEYEVIANLKEAMAVCEQEQDYQSRDLLLKILADTEEDHAYWLEKQLG
LIEKIGLQNYLQSQMS

SEQ ID NO:20

MDSGEIRATPARAAFLRPGKPEECYFFQGDQYIRMLITPGATNDKLLYGPAKIMDEWPSLKQAGFNSIDA
CLPSPKDDSEVYFFSGDQYCLIKVVPESSNDKIITGPKSIADYWPSLKKAGFTTLEEVFPSPRGDGETYC
FKDSNYCRIKFVPGTLDESLMNGPTDIQAGWPSLKQVGFSSIDVAVVNYKDPSQVYCFNGNQYARIHVVP
GTSDDTVIDGPHDVASRWPALKQAGFY

SEQ ID NO:21

TKPGYINAAFRSSKNNEAYFFINDKYVLLDYAPGSSRDKVLYGPTPVRDGFKSLNQTIFGSYGIDCSFDT
ENNEAFIFYENFCALIDYAPHSKKDKIILGPKKIADVFPFFEGTVFESGIDAAYRSTRGKEVYLFKGDQY
ARIDYGSNSMVNKEIKSISSGYPCFRNTIFESGADAAFASHKTNEVYFFKDDHYARVKVTPGGKLAIMDG
VREIVDYWPSLKDIVPL

FIG. 7A continued

SEQ ID NO:22

MARALRVPVALWLLGLCWSLAKAHPLARAPELGHGVEGGNVAKPDPEVTERCSDGWGFDATTLDEHGNML
FLKGEFVWKGHAWARQLISERWKDAPSPVDAAFRYDRNSVLLIKGDKFWVYPPEKGEEYPKLLQEKFPGI
PFPLDAAVECHRGECSHEGVFFFQGNHTWFWDFSTKTIKKRSWPAVGNCSSAIRWLNRYYCFRGNKFLRF
DPVTGEVNSTYPRDVRDYFMSCPNRGHAHRNATQHMDKRCSPHLVLSALLSDNHSATYAFSENHYWRLDS
SRDGWHSWRIEHLWPQGPSTVDAAFLWDKKLYLIQGTQVYIFLTRAGYTLVKDYPKQLEKEFGSPDGVCL
HSVDAAFTCPGSSQLYIMAGQKLWRLDLNLGAQATWTELPWLHTKVDGALCTEKSLGPHSCSANGLGLYL
VQGPNLYCYKDVEELSKTKDLPQAQRMNSLLGCAPHQHS

SEQ ID NO:23

MTVYTNTSLKAELNERGWRLTPQRETILHIFQELPQGEHLSAEDLYHRLEADGEGISLSTIYRTLKLMAR
MGILRELELGEGHKHYEINQPYPHHHHHLICVKCNSTIEFKNDSILKIGAKTAQKEGFHLLDCQMTIHAV
CPKCQRALMPL

SEQ ID NO:24

MDIQNMPREQLGVCAEGNLHSVYLMFNANDNVESQLRPCIANVAQYIYELTDQYSDSAFNGFVAIGANYW
DSLYPESRPEMLKPFPAMQEGNREAPAIEYDLFVHLRCDRYDILHLVANEISQMFEDLVELVEEERGFRF
MDSRDLTGFVDGTENPKGRHRQEVALVGSEDPEFKGGSYIHVQKYAHNLSKWHRLPLKKQEDIIGRTKQD
NIEYESEDKPLTSHIKRVNLKDENGKSIEILRQSMPYGSLKEQGLMFISTCRTPDHFEKMLHSMVFGDGA
GNHDHLMHFTSALTGSSFFAPSLDFLMQFDN

SEQ ID NO:25

MPFETSPADTLCRSAGCPHLSGAHLGRGSLEKEPPEDKEAKELLWIRPDAPSRCSWQLGRPVADSPHCHA
ALVKSPKILPDILKKIGDTPMVRINKIGRNFGLKCELLAKCEFFNAGGSVKDRISLRMIEDAEREGTIKP
GDTIIEPTSGNTGIGLALAAAVKGYRCIIVMPEKMSTEKVDVLRALGAEIVRTPTNARFDSPESHVGVAW
RLRNEIPNSHILDQYRNASNPLAHYDITAEEILQQCDGRLDMLVASAGTGGTITGVARKLKEKCPGCKIV
GVDPEGSILAEPEELNQTEQTAYEVEGIGYDFIPTVLDRTVVDKWFKSNDEEAFAFARMLIAQEGLLCGG
SSGSAMSVAVKAAQELQEGQRCVVILPDSVRNYMSKFLSDKWMLQKGFMKEEEISVKRPWWWHLQVQELS
LSAPLTVLPTVTCEHTIEILREKGFDQAPVVDESGVILGMVTLGNMLSSLLAGKVQPSDQVCKVIYKQFK
QIYLTDPLGKLSHILEMDHFALVVHEQIQYRCHGESSKRQMVFGVVTAIDLLNFVATRERNQRTKPESAL
KLGGVGAEAQL

SEQ ID NO:26

MERPQPDSSMPQDLSEALKEATKEVHTQAENAEFMKNFQKGELTQEGFKLVMASLYHIYVALEEEIERNK
ENPVYTPLYFPEELHRRASLEQDMAFWYGPRWQEAIPYTQATKRYVQRLQEVGRTEPELLVAHAYTRYLG
DLSGGQVLKKIAQKALNLPSSGEGLAFFTFPNIASATKFKQLYRSRMNTLEMTPEVRQRVLDEAKTAFLL
NIQLFEELQGLLTQKAKDHDPLQAPELHRRAGSKVQDLAPTKASRGKPQPSVLSQAPLLRWVLTLSFLVA
TVAVGLYAM

FIG. 7A continued

SEQ ID NO:27

MKNILKVFNTTILALIIIIATFSNSANAADSGTLNYEVYKYNTNDTSIANDYFNKPAKYIKKNGKLYVQI
TVNHSHWITGMSIEGHKENIISKNTAKDERTSEFEVSKLNGKIDGKIDVYIDEKVNGKPFKYDHHYNITY
KFNGPTDVAGANAPGKDDKNSASGSDKGSDGTTTGQSESNSSNKDKVENPQTNAGTPAYIYAIPVASLAL
LIAITLFVRKKSKGNVE

SEQ ID NO:28

MAFSVNYDSSFGGYSIHDYLGQWASTFGDVNHTNGNVTDANSGGFYGGSLSGSQYAISSTANQVTAFVAG
GNLTYTLFNEPAHTLYGQLDSLSFGDGLSGGDTSPYSIQVPDVSFGGLNLSSLQAQGHDGVVHQVVYGLM
SGDTGALETALNGILDDYGLSVNSTFDQVAAATAVGVQHADSPELLAA

SEQ ID NO:29

MSKSIYEQYLQAKADNPGKYARDLATLMGISEAELTHSRVSHDAKRLKGDARALLAALEAVGEVKAITRN
TYAVHEQMGRYENQHLNGHAGLILNPRNLDLRLFLNQWASAFTLTEETRHGVRHSIQFFDHQGDALHKVY
VTEQTDMPAWEALLAQFITTEIPELQLEPLSAPEVTEPTATDEAVDAEWRAMTDVHQFFQLLKRNNLTRQ
QAFRAVGNDLAYQVDNSSLTQLLNIAQQEQNEIMIFVGNRGCVQIFTGMIEKVTPHQDWINVFNQRFTLH
LIETTIAESWITRKPTKDGFVTSLELFAADGTQIAQLYGQRTEGQPEQTQWRDEIARLNNKDIAA

FIG. 7B

*Amino acid sequences of proteins listed in TABLE 1B*

SEQ ID NO:30

MGSSHHHHHHSSG
EAAGAGTPTQPPAPHPAVAPLAFLLGKWRGEGEGSFPTISSFRYGEELLFSHHPSKPVISYAQKTWKAAS
GEPMHAESGYWRPRPDGTVEVVIAQSTGLAEIQKGSYDAEKKMVTLQSELVGNASKVKQITRAFQVADGE
LSYIVQMATITTSLQPHLKALLKKI

SEQ ID NO:31

MGSSHHHHHHSSG
PALIETCVPATSTQETISRKYDVTQNGFLPSSAPLRRLTDPYYALWELLAEKLPELLERKLLRYIVDSSQ
VLSTDRLQSEEEWRRAYVVLVFLAHGYIWGGDRPSEVLPPQITVPLLKLAEHFDLPPCATYAGLVLWNFE
TLNNDSDFSDPDNLRAINTFTGTESESWFYMISVALEAQSAWVMPLMVDAIEATHSRDYAKMKKGLEQII
IAIKKMDELLKRMYEKCDPALFYDKIRPFLAGSANMEAAGLPNGVFYDEGDGKGSWRKLMGGSNGQSSLI
QFFDVVLGVEHTGGADKASVPKVCPVSGMATEESTSGCPVSAGKEKNMGYHEKVRAYMPEPHRRFLRSLA
RMGSLQAFASTPQPDAEFEQVKELYQLACKTMGDFRCTHIQVVTKYIIIQARKQPVGETLNLAKASSASD
GSDLKGTGGTSLAAFLKQSRDESYEAGRVPDQPAPGVSSEYAVM

SEQ ID NO:32

MGSSHHHHHHSSG
LQGRIAAVDQRTSVRRSGMHVRRDARAGSVRSAAAVLWARPDAQGFLPAIEPQVRIQLDDPAVQEWEQAL
HELPGAFGAGSGTQLRERLRRLPPFPTDRLLPPWTSPGRIPSLQPPLACIGGGGTGGSRSGGGGGSGGGG
MTGDVEDRLLLPAQDAADHPPAGAVEPEAPTSGGFLDDGNAWRAYLVLSFLAHAYVWCEPGPPPAVLPAV
LAVPWARVAAAVGMPPILTYATYNLYNWRRLNPELPPVLQNLSSINNFLGGPDEEWFRLVHVDIETRAGP
AVAGLARLQQAAAQDDAGAVLMGLSAISESLRAMQTTLARIGECCDPDQYYSRVRPPIAGWRNNPLLPYG
LVYEGVYGGAPVQLYGATGAQSSVVPAFDRVLDIRHEQGRLRDYLGTMVAHMPPPHRAFLAALAAANNNT
GTGTGNRTNSGASTNSSGGAGRGQDGGAGQPVAAANVRAYVLAAAATGSGHPRGGELRDAYDCTVGELDR
FRSLHRSVAQRYIVQPATATTTAPASTATATTTAPASASASASTAASTSTSAHLHTHATSITAVGSTAAG
AASPSAPPPPPPAPLPTRGGVGQPDGLLASGTLASGVAAAVGTAVETAVALAGVTGTGGSDVIPALTAFR
DATRRHKIARSD

SEQ ID NO:33

TTMTGQISAEAQRVDAPLTQSATFLVLSLLDRPDTVHTVRSTLANLESLSKNVSIRDPSASFTCTTGIGS
DAWDRLTGHPRPAELHPFPEVKGARHTAVSTPGDLLFHIRSERRDLCFEFERQLLDCLGDTIVVVDETVG
FRYFDLRDLLGFVDGTANPVGAAVPSSTLVAEEDVAACGGSYIVVQKYVHDIKTWRALSVEQQEAIIGRT
KVENVELDDAPADHQQAHKSLSTITDENGVEHSILRDNMPFGSPGSGEFGTYFIGYSRRLWVIEQMLQRM
FVGSPPGSHDRLLDFSTPLTGTTFFAPSLDFLRNLSPE

SEQ ID NO:34

MGSSHHHHHHSSG
KASSRAQAVDGPLTQSASFVVLTVADGAEAIKTVRSVLSGLSGVAKSVGMRDSTGSLACTVGIGSRVWDK
LMGMPRPAELRAFKEIKGKRHTAVSTPGDLLLHIRSDRRDICFEFERQVMKQLGSAVQVQDATVGFRYFD
LRDLLGFVDGTANPVGPAVPDAVLVAEEDDERSAGGSYIVVQKYHHNLEAWEKLSTEKQEAVIGRTKLDN
MELDDAPAAAQKSHKTLATIEDEEGNEHDILRDNMPFGSPGTQEFGTYFIGYSRRLWVVERMLERMFIGD
PPGLHDGILDFSEAKTGSVFFAPSADVLAGLD

FIG. 7B continued

SEQ ID NO:35

MGSSHHHHHHSSG
ERLSIVPIIARSGHTTEPIPLSKIGHRTPILSPFIHDHHHRPLHTAPTPSHPPTMSRTSLRPQRVDAPLT
QFATFLVLTLDPSPPSLSTVRTTLASLSDLTKNITIRDPSAHFTCTVGIGSTIWDDLTRLPRPSELRPFP
EIPGPKHTAISTPGDLLFHIRSERRDLCFEFERQLLDRLGHTVTVVDETEGFRYFDMRDLLGFVDGTANP
VGPAVPDAVLITKNTDPAAAGGSYIVIQKYLHDLSAWKSLPIEHQERIIGRTKLENIELADAEDGAQQSH
KSLATIEDENGEEYAIVRDNMPFGAPGKGEFGTYFIGYTARLWVIEKMLERMFVGEPRGKYDRILDFSVP
KTGGTFFAPGGGVLDSLDDH

SEQ ID NO:36

MGSSHHHHHHSSG
TTPAPPLDLNNIQGDILGGLPKKTETYFFFDVTNVDRFKANMTQFIPHVKTSAGIVKDREAIKEHKRQKR
PGLVPMAAVNVSFSHLGLQKLGITDDLSDSSFTTGQRKDAEVLGDPGTKNGDTFTPAWEAPFLKDIHGVI
FVAGDCHASVHKKLDEIKHIFGVGTSHASISEVTHVRGDVRPGQVSAHEHFGFLDGISNPAVDQFDQNPF
PGQDSIRPGFILAKENGDSRAAARPDWAKDGSFLTFRYLFQMVPEFDDFLESNPIVLPGLSRKEGSELLG
ARIVGRWKSGAPIEITPLKDDPKLGADAQRNNNFDFGDSLVRGDQTKCPFAAHIRKTYPRNDLEGPPLNA
DIDNRRIIRRGIQFGPEVTSQEHHDKKTHHGRGLLFVCYSSSIDDGFHFIQQSWANAPNFPVNAVTSAGP
IPPLDGVIPGFDAIIGQKVGGGIRQISGTNPNDPTTNITLPDQDFVIPRGGEYFFSPSISALKTKFAAGV
ASSAPQAQAPIST

SEQ ID NO:37

MGSSHHHHHHSSG
RKESNRRSDQQKKSPGIETETPKKMEGGGAPAPAAPPPAPHPAVAPLAFLLGKWRGEGEGSFPTISPFRY
GEELVFSHHPSKPVISYTQRTWKPASGEPMHAESGYWRPRPDGSVEVVISQSTGLAEVQKGSFDAEKKTL
TLQSELVGNASKVKQITRAFQLVDGELSYVVQMATITTSLQPHLKALLKKI

SEQ ID NO:38

MGSSHHHHHHSSG
NQLQQLQNPGESPPVHPFVAPLSYLLGTWRGQGEGEYPTIPSFRYGEEIRFSHSGKPVIAYTQKTWKLES
GAPMHAESGYFRPRPDGSIEVVIAQSTGLVEVQKGTYNVDEQSIKLKSDLVGNASKVKEISREFELVDGK
LSYVVRMSTTTNPLQPHLKAILDKL

SEQ ID NO:39

MGSSHHHHHHSSG
TARSQATNTQKRPKVQCSATTKQLLFNQVTPDRAFLPAQDPLLRLPPGLQAYEDALQELPKLTLGSPGFL
RQTLQDLPCFDLQQLPALASCDTAQLLQQLPPACQCYTAAAGTSSSSSSSPQQSTADVLRSFPSCDAQLW
RAYMVLAFLTHGFLWCDGPGVPSVLPHLLAGFLWCDGPGVPSVLTQLLAQPFAAVSAAIGMPPVLTYATY
NLMNWRRLDPAAPLELGNICCQHNFFGGMDEEWFRLIHVAIEAAAAPAIAALQPLQQAALQHDAAAMELH
FAAITSALQAMQELLARMGERCDPYVYYKRVRVPMSGWRNNEALPQGLVYEGLWGNQPQQLYGETGAQST
VVHALDAALGIQHTKGWMQAYLTDMRAHMPPSHRAFLHQLEQEPSVRDAVQALAQTTTSSSSSNNNSSGS
NKSSSSSSLVEAYDAAIAELERFRSQHRAFAIAYIAQWSKKEAKEVGTGGSDFVPALSAYKDATAAHKLA
GSSSSSRGCPLHS

FIG. 7B continued

SEQ ID NO:40

MGSSHHHHHHSSG
LPPIPALADYGISADHGFLPPEPPLEILPDPYYAKWEWVVSNLQALLTSRRIREVVDHMSTLSTSYLQTE
NEWRRAYVVLVFMLHGYVWGGSKPAEKIPPQLTVPLFDVCEHLGLPPVATYAGVCLWNYKPIFPEEPIDD
LRNLDTVNTFTGSLDEKWFYLVSVAIEARGAPSIPLVLQAIAAARAGNSLVVTECLQRLAEVLDEVGSLL
ERMYEHCDPYVFYHRIRPYLAGSKNMADAGLPHGLLYDNGSGQPEYRQYGGGSNAQSSLIQFFDIALGIE
HRPTGETRPSSSPVKDEKEGVAGAPRHGFIQEMRTYMPAAHRRFLEHINAVANIRQYVEARRSDKALCIA
YDACLSMLRAMRDKHIQIVSRYIIIQSRDARPSRPARATSPKRAINLATARHGEKPDSKKLRGTGGTALI
PFLKQARDETGEPAIDAWARRLLSTGPSESSFAALSKVDEDHDGHLQVVGLSGTWAADDSEGGICHW

SEQ ID NO:41

MGSSHHHHHHSSG
RSMQPLILFVLGSLAIIVFWKSIVQPFIQSWLQTLPKSDIRKEKSDAIKDLAEHHEVAEILSELIQKDGA
GSWPPNANHAHTEWPLCIQPYREIYLEMAPLLPQPEPSLDDEVNASRISEFRQRYRDLLSERVDLVEVKK
LMDMAEADRWVEFPRDVYNAFYCCIASTRHAYRWATIPVVKVAQLEKVVELPVELTMPWESMQRHFGCPS
DGGNVTCNLLLNFDKTGSYIYKINTGMAPRILAAEEAFSRIFYDLESLSLPVYHDMAQAIIALDRGDTAA
CARHVASITAQMQGVIATYTTKLHDKFIAHSIWLSRIQGFFGWGAGHYNTETNEWEKYDGLSGNQLLLFP
AMDAFLGIEQYLSQRDQEMSVPRRQRELCHALRKHSFRARLAKMDGDIHVAEILHNFDMILKQLRLFRAA
HRTRAKTYLSQPAPERLPMTAGKSLLKPSIEDSFEFLDKFMVRRLGQTV

FAMILY OF HEME BINDING PROTEINS THAT INCREASE CHELATED IRON CONTENT AND IMPROVE FLAVOR OF NUTRITIONAL SUPPLEMENTS AND FOOD PRODUCTS

RELATED APPLICATION

This patent disclosure claims the priority benefit of U.S. provisional patent application 63/333,901, filed May 9, 2022. The priority application is hereby incorporated herein by reference in its entirety for all purposes.

FIELD OF THE INVENTION

This patent disclosure relates generally to the identification of natural sources of new food ingredients. It provides a family of proteins that contain or are capable of capturing a heme or other porphyrin for the purpose of carrying an iron atom in nutritional supplements and food products.

BACKGROUND

Iron deficiency occurs when someone lacks enough iron to supply metabolic needs. Iron is present in virtually all cells in the human body. It has several important functions, such as carrying oxygen to the tissues from the lungs as a key component of the hemoglobin protein, acting as a transport medium for electrons within the cells in the form of cytochromes, and facilitating oxygen requiring enzyme reactions in various tissues. Too little iron can interfere with these vital functions and can have dire health consequences.

Dietary factors may affect iron absorption. When loss of iron is not sufficiently compensated by intake of iron from food, iron deficiency develops over time. Uncorrected, it leads to iron-deficiency anemia and other hematologic abnormalities Anemia is characterized by inadequate circulating levels of red blood cells (erythrocytes) or hemoglobin. In the absence of sufficient iron, production of hemoglobin containing proteins is reduced. Left untreated, it can cause problems like an irregular heartbeat, pregnancy complications, and delayed growth in infants and children that could affect their cognitive development and behavior.

Anemia can be treated with iron supplements. Dietary intake of 5 to 15 mg per day is recommended, the top end for children and women of child-bearing age. Dietary supplements that are currently marketed are typically ferrous sulfate, ferrous gluconate, or amino acid chelate.

SUMMARY

This disclosure provides materials and methods for improving the nutritional value of food products by increasing the content of chelated iron. Heme iron has higher bioavailability than nonheme iron, and other dietary components have less effect on the bioavailability of heme than nonheme iron. Murray-Kolbe L E et al., in: Coates P M, et al., eds. *Encyclopedia of Dietary Supplements.* 2nd ed., 2010; Hurrell R, Egli et al., Am J Clin Nutr 2010; 91:1461S-7S. For this reason, the heme containing proteins of this disclosure constitute a superior approach to including iron in food products and nutritional supplements.

A family of proteins that contain or bind heme (designated as PX90 proteins) are described in the sections that follow. Before the making of this invention, the PX90 proteins listed below and related homologs have not been used as additives either as nutritional supplements or in food. Subcategories of PX90 proteins are structurally related to THAP4-like heme-binding beta-barrel domain containing proteins, indoleamine 2,3-dioxygenase 1 (IDO1), DyP-type peroxidase, hemopexins, and ferritins.

PX90 proteins can be prepared by recombinant expression, and then included or added into nutritional supplements or food products during manufacture or preparation. The presence of a recombinantly produced protein in a comestible product can be determined by the history of manufacture, and also by certain characteristics of the comestible itself. Specifically, the PX90 protein in the supplement or product may be a recombinantly altered form of a naturally occurring protein. Alternatively or in addition, the comestible will be devoid of most other protein components or a characteristic protein profile of the biological source in which the PX90 protein occurs naturally.

The inclusion of a heme binding protein in plant-based food products either coincidentally or by intention may also impart a meat-like flavor or aroma. The foods and supplements of this disclosure are suitable for consumption as regular components of a healthy diet. The bioavailable iron in food products and supplements put forth in this disclosure is especially beneficial for consumers who have manifestations of iron deficiency, low blood hematocrit, anemia, and other hematological abnormalities.

Food products especially suitable for inclusion of a PX90 protein include those that are already marketed with supplemental iron. Infant formula can be formulated with a PX90 protein rather than an iron salt. Flour can be formulated with a PX90 protein rather than an iron salt—or alternatively, by genetically modifying the wheat or other grain milled used to make the flour so that it expresses a PX90 protein. This way, the grain will already contain the added heme binding protein before it is milled: no additional iron needs to be added during manufacture. Using a PX90 protein in place of iron salts in these foods would improve bioavailability of the iron upon consumption, and help stabilize physiological iron levels.

Aspects, embodiments, features, and characteristics of the invention, its products, their manufacture, and their use are described in the sections that follow, the accompanying drawings, and the appended claims.

BRIEF DESCRIPTION OF THE DRAWINGS

FIG. 2A is a depiction of D25 bound to the porphyrin meso-tetra-(4-sulfonatophenyl) porphyrin (TPPS$_4$), determined from the crystallographic structure at 1.8 Angstroms. FIG. 2B shows DC25 (ligand) binding affinity with different concentrations of TPPS$_4$ analyte in range of 0.1 to 12.5 μM by surface plasmon resonance (SPR).

FIGS. 3F and 3G show the predicted structure of DyP-peroxidase from Cellulomonas *bogoriensis*. DyP-peroxidase is typically a dimer with the active site buried in between the alpha helices and the beta sheets. Adapted from MH Habib et al., Molecules 2019, 24, 1208; doi:10.3390.

FIGS. 4A and B show the structure of a ferritin from Chaetopterus, and its ion binding sites: (a) the crystal structure of a ferritin cage; (b) three ferritin subunits. Adapted from P. Chen et al., Nature Sci Rep. 2020 Mar. 4; 10(1):4033. FIG. 4C shows the crystal structure of human indoleamine 2,3-dioxygenase 1 (IDO1) in complex with ferric heme and small molecule inhibitor MMG-0358. PDB accession no. 6R63, Roehrig, U. F. et al., 2019.

FIG. 4D shows the predicted structure of UPF0678 fatty acid-binding protein-like protein from *Panicum miliaceum*, which contains a THAP4-like heme-binding beta-barrel domain. UniProt Accession No. AOA3L6SSU6. FIG. 4E shows the predicted structure of another THAP4-like heme-binding beta-barrel domain-containing protein from *Oryza punctata* (red rice): UniProt. Accession no. A0A0E0JMF. Where the heme binding portion is represented by the barrel domain (the beta-pleated sheets), this portion can be expressed without the extended hydrophilic N- or C-terminus.

FIG. 6 shows the amino acid sequences of the ten plant hemoproteins that have a hemopexin fold, listed in TABLE 2.

FIGS. 7A and 7B show the amino acid sequences of the PX90 hemoproteins listed in TABLES 1A and 1B. The listed proteins are of current interest as nutrition improving ingredients of food products.

DETAILED DESCRIPTION

Unity of Invention

Figure 1A:
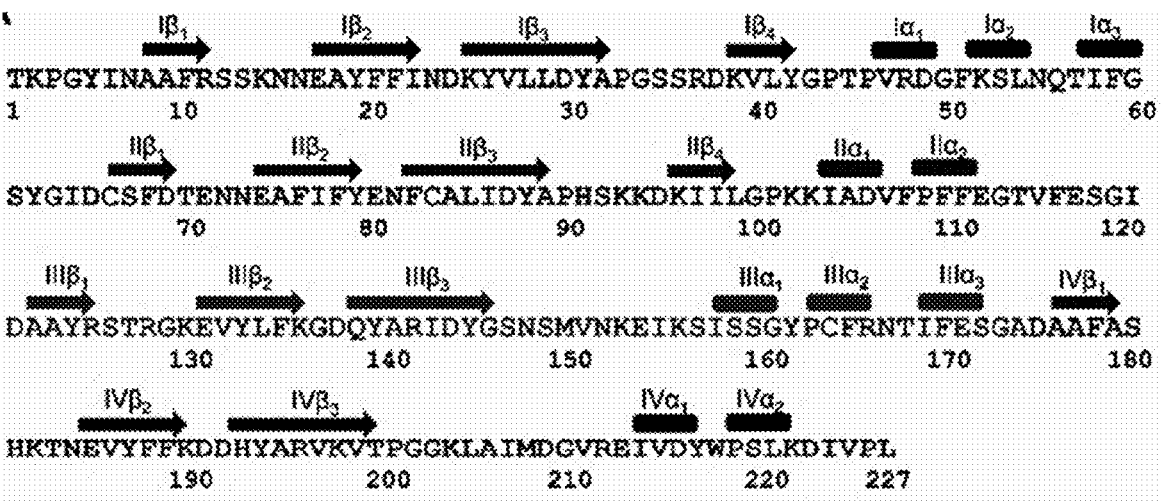
FIGS. 1A and 1B show an annotated version of the amino acid sequence (SEQ. ID NO:1) and the crystal structure of a hemopexin fold protein from grass pea. Adapted from V. Gaur et al., Plant Physiol. 2010, 152:1842.

The PX90 proteins of this disclosure is a family of heme binding proteins that have been identified and established as suitable additives to increase chelated iron content of nutritional supplements and food products. The listed proteins were selected from over one point three million protein candidates. They share the following characteristics:

- occur in nature as a protein monomer or self-polymer (not a heterologous polymer);
- not a membrane protein;
- less than about 800 amino acids in length;
- have a three-dimensional structure that forms a single globular domain;
- safe for human consumption;
- not immunogenic or allergenic;
- do not have undesirable enzyme activity;
- can easily be recombinantly manufactured in yeast and other cell cultures;
- spontaneously incorporate heme and iron when expressed using common laboratory expression systems without enhanced expression of heme building enzymes; and
- not currently used and have not previously been developed for use as a recombinantly produced additive for nutritional or food products for the purposes stated herein.

Subcategories of PX90 proteins are structurally related to THAP4-like heme-binding beta-barrel domain containing proteins, indoleamine 2,3-dioxygenase 1 (IDO1), DyP-type peroxidase, hemopexins, and ferritins. Of particular interest are proteins that are expressed naturally in plants or fungi already part of the human diet in at least some cultures or contexts.

As used in this disclosure, the term "PX90 protein" refers to a protein that has any of the structural features of a porphyrin binding or heme containing protein (or a porphyrin binding or heme containing fragment thereof) as put forth in this disclosure, characterized as having a binding affinity of at least $1 \times 10^6$ M$^{-1}$ for a heme or other porphyrin with iron binding or storing activity. In some examples, the affinity may be at least $1 \times 10^8$ M$^{-1}$, $1 \times 10^{10}$ M$^{-1}$, or $1 \times 10^{12}$ M. Individual proteins may be identified as having an amino acid sequence that is at least 80%, 90%, or 95% identical to any of SEQ. ID NOS:1 to 43 or a heme binding portion thereof, or as at least 60%, 70%, 80%, or 90% identical to another protein in the same structural subcategory, or heme binding portion thereof.

Heme binding portions can be determined by expressing the protein with successive truncations at the N- and/or C-terminus, until a limit fragment is obtained that retains heme binding activity. Comparisons between amino acid sequences is made using the BLAST algorithm (SF Altschul et al., 1990; J. Mol Biol. 2015:403-410). Depending on context, PX90 proteins may not include the following: hemoglobin, myoglobin, leghemoglobin, non-symbiotic hemoglobin, chlorocruorin, erythrocruorin, neuroglobin, cytoglobin, protoglobin, truncated 2/2 globin, HbN, cyanoglobin, HbO, Glb3, cytochrome, Hell's gate globin 1, bacterial hemoglobin, ciliate myoglobin, and flavohemoglobin.

A porphyrin binding protein described and claimed below may or may not contain a porphyrin such as a heme molecule. Depending on context, a heme molecule may or may not be complexed with an iron atom.

Hemoproteins Generally

Hemoproteins have diverse biological functions including the transportation of diatomic gases, chemical catalysis, diatomic gas detection, and electron transfer. The heme iron serves as a source or sink of electrons during electron transfer or redox chemistry. In peroxidase reactions, the porphyrin molecule also serves as an electron source, being able to delocalize radical electrons in the conjugated ring. In the transportation or detection of diatomic gases, the gas binds to the heme iron. During the detection of diatomic gases, the binding of the gas ligand to the heme iron induces conformational changes in the surrounding protein. Milani, M. (2005) J. Inorg. Biochem. 99 (1): 97-109.

In general, diatomic gases only bind to the reduced heme, as ferrous Fe(II) while most peroxidases cycle between Fe(III) and Fe(IV) and hemoproteins involved in mitochondrial redox, oxidation-reduction, cycle between Fe(II) and Fe(III). Hemoproteins achieve their functional diversity by modifying the environment of the heme macrocycle within the protein matrix. For example, the ability of hemoglobin to deliver oxygen to tissues effectively is due to specific amino acid residues located near the heme molecule.

Biological functions of hemoproteins include using the central iron atom in oxygen retention and transport: for example, hemoglobin, myoglobin, neuroglobin, cytoglobin, and leghemoglobin. Another function is using the central iron as an electron holder to catalyze redox reactions: for example, cytochrome P450, cytochrome c oxidase, ligninases, catalase and peroxidases. Participants in the electron transport chain in mitochondria include cytochrome a, cytochrome b, cytochrome c, and some of the cytochrome loading enzymes. Participants in the sensory system include FixL, an oxygen sensor, CooA, a carbon monoxide sensor, and soluble guanylyl cyclase.

Selecting PX90 Hemoproteins for Dietary Supplementation

Any hemoprotein referred to in this disclosure can in principle can be a candidate as a food ingredient, depending on context and the user's objective. The owners of this technology identified many of the candidates listed below by computer calculation, mapping heme binding proteins by embedding distance, based on sequence and either known crystal structure or predicted three-dimensional structure. During the course of this project, one point three million candidates were identified for further assessment. Candidates were deprioritized if they existed in nature principally as heterodimers or membrane proteins, if they were more than 800 amino acids in length, if they were for some reason or another considered to be inedible, immunogenic, or allergenic, if they were not easily expressible in *Pichia pastoris* or other host cells, or if they had enzyme activity that for one reason or another was undesirable.

The hemoproteins listed in TABLE 1A were selected as top candidates because of their stability and ease of expression.

A second selection of hemoproteins is listed in TABLE 1B. Candidates were selected from:

folds reported to independently bind heme or its derivatives (Smith, LJ. (2010) Proteins 78(10): 2349-2368);
proteins with sequence patterns that delineate families of heme-binding proteins (Mistry, J. et al. (2021) Nucleic Acids Res. 39(1): D412-D419); and proteins that may co-crystalize with a heme or heme-like molecule, based on the RCSB database (Berman, H M. et al. (2000) Nucleic Acids Res. 28(1): 235-242).

Rational candidate selection was done using different combinations of diverse filtering steps that included the following:

baked on taxonomy (for example, proteins that originate in plants or fungi);

structure simplicity (for example, proteins that have a single, rather than multiple globular domains);

amenability to standard empirical screening (for example, proteins that are not annotated as transmembrane proteins); and relevance for food product applications (for example, the protein originates in an edible organism).

The set of selected proteins was expanded by identifying remote homologs of candidates already selected by way of sequence embeddings (Rives A et al. (2021) Proc Natl Acad Sci USA 118(15): e2016239118). A plurality of candidates were manufactured by recombinant expression and tested for heme binding.

FIGS. 7A and 7B show amino acid sequences of proteins listed in TABLES 1A and 1B, respectively. The sequences shown in FIG. 7B include an added 13-residue HIS tag at the N-terminus that is used for affinity purification in high throughput screening. The protein is usually made without the tag for inclusion in products intended for human consumption.

TABLE 1A

| | | | | PX90 hemoproteins that enhance nutrition in food products | | |
|---|---|---|---|---|---|---|
| SEQ ID NO: | UniProt accession | kingdom | source organism | protein name | Pfam family | domain name |
| 11 | O64527 | plants | *Arabidopsis thaliana* | Peroxynitrite isomerase | PF08768 | THAP4-like heme-binding beta-barrel domain |
| 12 | O04797 | plants | *Lepidium virginicum* | Water-soluble chlorophyll protein | PF00197 | Kunitz STI protease inhibitor |
| 13 | A8P0V4 | fungi | *Coprinopsis cinerea* | CBM1 | PF16010 | Cytochrome domain of cellobiose dehydrogenase |
| 14 | A0A1Y2TH07 | fungi | *Hypoxylon Cloroperoxidase* | Cloroperoxidase | PF01328 | Peroxidase, family 2 |
| 15 | B9W4V6 | fungi | *Agaricus aegerita* | Aromatic peroxygenase | PF01328 | Peroxidase, family 2 |
| 16 | Q43206 | plants | *Triticum aestivum* (Wheat) | Catalase | PF00199 | Catalase |
| 17 | A0A0A0Y4H8 | plants | *Trachycarpus fortunei* | Peroxidase | PF00141 | Heme peroxidase |
| 18 | P19975 | plants | *Pisum sativum* (Garden pea) | Ferritin | PF00210 | Ferritin-like domain |
| 19 | P24602 | cyanobacteria | *Synechocystis* sp. | Ferritin | PF00210 | Ferritin-like domain |
| 20 | A0A067NJU2 | fungi | *Pleurotus ostreatus* (Oyster mushroom) | Hemopexin | | Hemopexin-like domain |
| 21 | D4AEP7 | plants | *Lathyrus sativus* (White vetchling) | Hemopexin | PF00045 | Hemopexin |
| 22 | Q3SZV7 | mammals | *Bos taurus* | Hemopexin | PF00045 | Hemopexin |
| 23 | Q9L3F6 | cyanobacteria | *Nostoc* sp. | FurA | PF01475 | Ferric uptake regulator family |
| 24 | Q8EIU4 | bacteria | *Shewanella oneidensis* | DyP-type heme-dependent peroxidase | PF04261 | DyP-type peroxidase family |
| 25 | F1MEW4 | mammals | *Bos taurus* | Cystathionine beta-synthase | PF00291 | Pyridoxal-phosphate dependent enzyme |
| 26 | Q5E9F2 | mammals | *Bos taurus* | Heme oxygenase 1 | PF01126 | Heme oxygenase |
| 27 | Q8KQR1 | bacteria | *Staphylococcus aureus* | Iron-regulated surface determinant protein C | PF05031 | Iron Transport-associated domain |
| 28 | Q54450 | bacteria | *Serratia marcescens* | Hemophore HasA | PF06438 | Heme-binding protein A (HasA) |
| 29 | P31517 | bacteria | *Yersinia enterocolitica* | Hemin transport protein HemS | PF05171 | Hemein-degrading HemS.Chux domain |

TABLE 1B

| SEQ ID NO: | UniProt accession | kingdom | source organism | protein name | Pfam family | domain name |
|---|---|---|---|---|---|---|
| | | | | Additional PX90 hemoproteins that enhance nutrition in food products | | |
| 30 | A0A3L6SSU6 | plants | *Panicum miliaceum* | upf0678_fatty_acid-binding_protein-like_protein | PF08768 | THAP4-like heme-binding beta-barrel domain |
| 31 | W3WJR4 | fungi | *Pestalotiopsis fici* | (uncharacterized protein) | PF01231 | Indoleamine 2,3-THAP4 |
| 32 | A0A2K3CPS1 | plants | *Chlamydomonas reinhardtii* | (uncharacterized protein) | PF01231 | Indoleamine 2,3-dioxygenase |
| 33 | A0A0U1M210 | fungi | *Talaromyces islandicus* | (uncharacterized protein) | PF04261 | DyP-type peroxidase family |
| 34 | A0A2C5YAJ0 | fungi | *Ophiocordyceps australis* | (uncharacterized protein) | PF04261 | DyP-type peroxidase family |
| 35 | A0A395GRN2 | fungi | *Aspergillus ibericus* | DyP-type_peroxidase | PF04261 | DyP-type peroxidase family |
| 36 | A0A6H0MBW1 | fungi | *Pleurotus sapidus* | DyP-type_peroxidase | N/A | N/A |
| 37 | A0A0E0JMF1 | plants | *Oryza punctata* | THAP4_heme-bd domain-containing protein | PF08768 | THAP4-like heme-binding beta-barrel domain |
| 38 | A0A654EQA7 | plants | *Arabidopsis thaliana* | At_nitrobindin_heme-binding_domain_protein | PF08768 | THAP4-like heme-binding beta-barrel domain |
| 39 | A0A383WJS5 | plants | *Tetradesmus obliquus* | To_uncharacterized_protein | PF01231 | Indoleamine 2,3-dioxygenase |
| 40 | A0A1L9UCU4 | fungi | *Aspergillus brasiliensis* | Ab_uncharacterized_protein | PF01231 | Indoleamine 2,3-dioxygenase |
| 41 | A0A3M7MCA5 | fungi | *Pyrenophora seminiperda* | Ps_indoleamine_23-dioxygenase | PF01231 | Indoleamine 2,3-dioxygenase |

The proteins listed in TABLE 1B were all identified as capable of expression in standard laboratory expression systems and capable of heme binding in vitro.

Proteins having a THAP4-like, heme-binding beta-barrel domain (PF08768) may catalyze detoxification reactions ("antioxidants"). Of particular interest are UniProt accession nos. A0A0E0JMF1 (SEQ. ID NO:37), AOA3L6SSU6 (SEQ. ID NO:30), AOA654EQA7 (SEQ. ID NO:38), and 064527 (SEQ. ID NO:11), which demonstrate excellent heme binding and expression.

Proteins in the family that comprises indoleamine 2,3-dioxygenase (PF01231) have been variously characterized as part of an enzyme superfamily, in some instances possibly evolved to act as transport proteins. Of particular interest are UniProt accession nos. AOA3M7MCA5 (SEQ. ID NO:41). W3WJR4 (SEQ. ID NO:31), A0A383WJS5 (SEQ. ID NO:39), AOAIL9UCU4 (SEQ. ID NO:40), and AOA2K3CPS1 (SEQ. ID NO:32).

Proteins in the family of DyP-type peroxidase (PF04261) are typically characterized as having a wide range of substrates. Of particular interest are UniProt accession nos.AOA2C5YAJO (SEQ. ID NO:34), AOA395GRN2 (SEQ. ID NO:35), AOA6HOMBW1 (SEQ. ID NO:36), AOAOUIM210 (SEQ. ID NO:33), and Q8EIU4 (SEQ. ID NO:24).

Hemopexin Fold Proteins

Hemopexin (1B-glycoprotein) is a plasma protein in mammals that has the highest binding affinity for heme. Its role is as a heme scavenger. Free hemoglobin in the blood is oxidized into met-hemoglobin, which then further disassociates into free heme along with globin chain. The free heme is oxidized into free met-heme, which is captured by hemopexin, which in turn binds to the receptor CD91 on hepatocytes or macrophages. The globin is captured by haptoglobin. The liver conjugates the heme to bilirubin for excretion, and retrieves the iron for reuse.

Hemopexins and their homologs fold in a characteristic way: a four-bladed p propeller structure having a pseudo four-fold molecular symmetry along a metal ion-binding central channel. Plants have homologs in places that carry porphyrins and/or iron: including but not limited to seeds, peas, and beans. A list of proteins with a hemopexin-like fold that may be suitable for inclusion in food is provided in TABLE 2. FIG. 6 shows the amino acid sequences of the listed proteins.

TABLE 2

| SEQ. ID NO: | GenBank protein accession | Source organism | Protein name | Reference |
|---|---|---|---|---|
| | | PX90 proteins containing a hemopexin fold | | |
| 1 | ALB2_LATSA | grass pea *Lathyrus sativus* | LS-24 | V. Gaur et al., Plant Physiol (2010) 152:1842-50 |
| 2 | 3OYO_A | cow pea *Vigna unguiculata* | CP4 | V. Gaur et al., Acta Cryst. (2011) F67:193-200 |
| 3 | AAA33641 | garden pea *Pisum sativum* | PA24, LS-24 | Ibid |
| 4 | CAA50008 | mung bean *Vigna radiata* | MBSA | Ibid |
| 5 | ABE87586 | barrelclover *Medicago truncatula* | hemopexin | Ibid |
| 6 | BAD06580 | rice plant *Oryza sativa* | OsHFP | T. Chattopadhyay et al., Biochem Biophys Res Commun (2012) 420(4):862-8 |
| 7 | 3V6N_A | chickpea *Cicer arietinum* | PA2 albumin | U. Sharma et al., Planta (2015) 241(5):1061-73 |

TABLE 2-continued

| | | PX90 proteins containing a hemopexin fold | | |
|---|---|---|---|---|
| SEQ. ID NO: | GenBank protein accession | Source organism | Protein name | Reference |
| 8 | P86782 | lentil *Lens culinaris* | PA2 albumin | A. Scarafoni et al., J Agric Food Chem (2011) 59(17):9637-44 |
| 9 | AHB89697 | oyster mushroom *Pleurotus ostreatus* | Ostreopexin | K. Ota et al., Biochim Biophys Acta (2013) 1834(8): 1468-73 |
| 10 | 6IX1_A | *Dolicos* | DC25 | SC Sharma et al., Sci Reports (2019) 9:19828 |

Figure 1B:
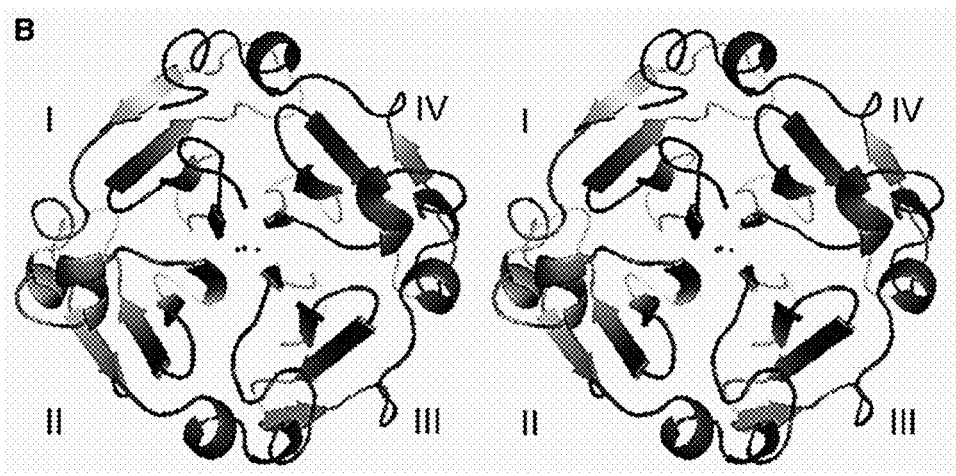

FIGS. 1A and 1B show the sequence (SEQ. ID NO:1) and the crystal structure of a hemopexin fold protein from grass pea. Adapted from V. Gaur et al., Plant Physiol. 2010, 152:1842-1850. It has a four-bladed beta-propeller structure having a pseudo four-fold molecular symmetry along a metal ion-binding central channel.

Figure 2A:
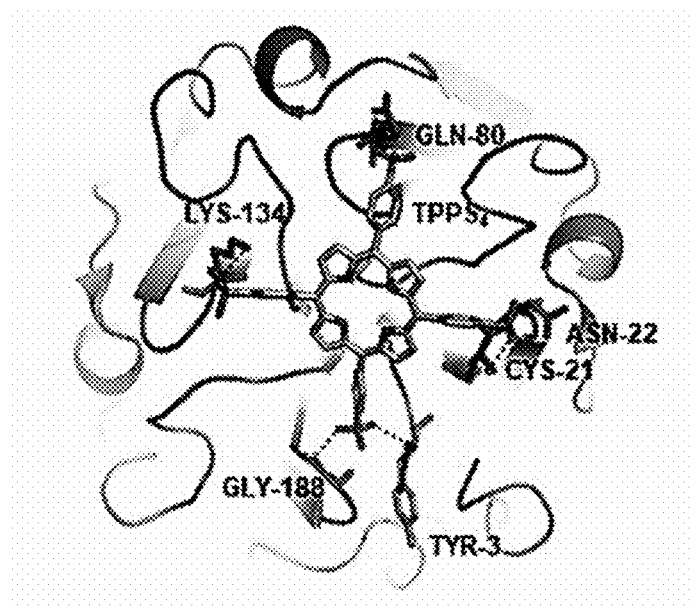
FIGS. 2A and 2B shows a high resolution structural and functional analysis of a hemopexin motif protein designated D25 from *Dolichos*. Adapted from SC Sharma et al., Sci. Reports 2019; 9:19828.
Figure 2B:
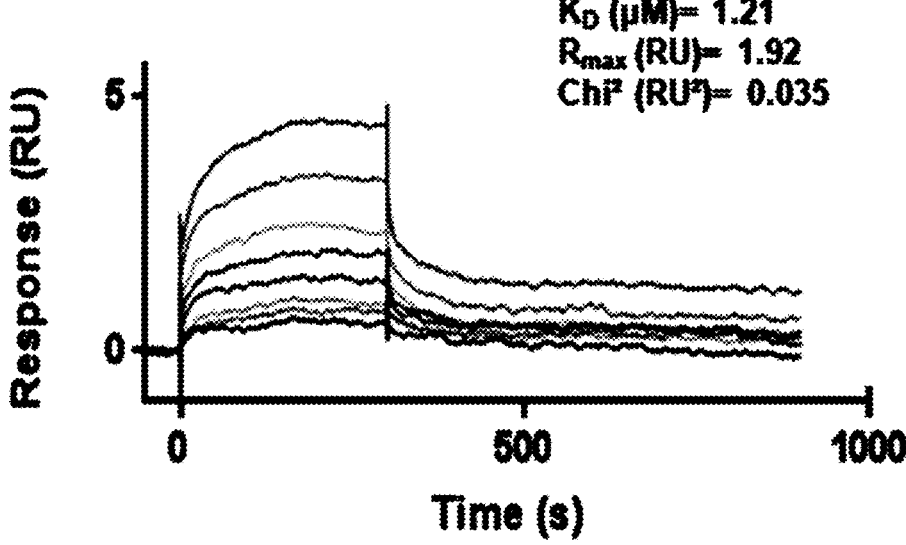

FIGS. 2A and 2B shows a high resolution structural and functional analysis of a hemopexin motif protein designated D25 from *Dolichos*. Adapted from SC Sharma et al., Sci. Reports 2019; 9:19828. FIG. 2A is a depiction of D25 bound to the porphyrin meso-tetra-(4-sulfonatophenyl) porphyrin (TPPS$_4$), determined from the crystallographic structure at 1.8 Angstroms. FIG. 2B shows DC25 (ligand) binding affinity with different concentrations of TPPS4 (analyte) in range of 0.1 to 12.5 µM by surface plasmon resonance (SPR). The protein is monomeric and highly thermostable in extreme conditions of pH and salt.

Comparative study of the protein with other seed hemopexins have revealed the presence of four conserved water molecules in between the blades which cross-link them and maintain the tertiary structure. The protein exhibits intrinsic peroxidase activity, which can be inhibited by binding of a heme analog. Identification of redox-sensitive cysteine and inhibition of peroxidase activity by iodoacetamide facilitated characterization of the possible active site. The peroxidase activity of DC25 may be responsible for rescuing germinating seeds from oxidative stress.

Peroxidases

Peroxidases are a class of enzymes having different structures and biological roles that catalyze the reaction ROOR'+2e$^-$+2H$^+$→ROH+R'OH. Some but not all families of peroxides contain hemes with a central iron atom.

Heme peroxidase from plants, bacteria, and fungi fall into three classes: Class I, the intracellular peroxidases, includes: yeast cytochrome c peroxidase in the mitochondrial electron transport chain, and bacterial catalase. Class II consists of secretory fungal peroxidases. Class III consists of the secretory plant peroxidases. The crystal structures of a number of these proteins show that they share the same architecture—two all-alpha domains between which the heme group is embedded.

The animal heme peroxidase superfamily include myeloperoxidase eosinophil peroxidase, lactoperoxidase; thyroid peroxidase; prostaglandin H synthase; and peroxidasin.

Catalase is found in nearly all living organisms exposed to oxygen, including bacteria, plants, and animals. The enzyme catalyzes the decomposition of hydrogen peroxide to water and oxygen. Catalase is typically a tetramer of four polypeptide chains, each over 500 amino acids long, containing four iron-containing heme groups. Haloperoxidases are peroxidases that are able to mediate the oxidation of halides. Mammalian haloperoxidases each contain a heme prosthetic group covalently bound by two ester linkages to aspartate and/or glutamate side-chains. The di-heme cytochrome c peroxidase family is a group of distinct cytochrome c peroxidases that contain two heme groups. These proteins have two domains, each containing one c-type heme group, with a calcium-binding site at the domain interface.

Figures 3A, 3B, 3C, 3D:
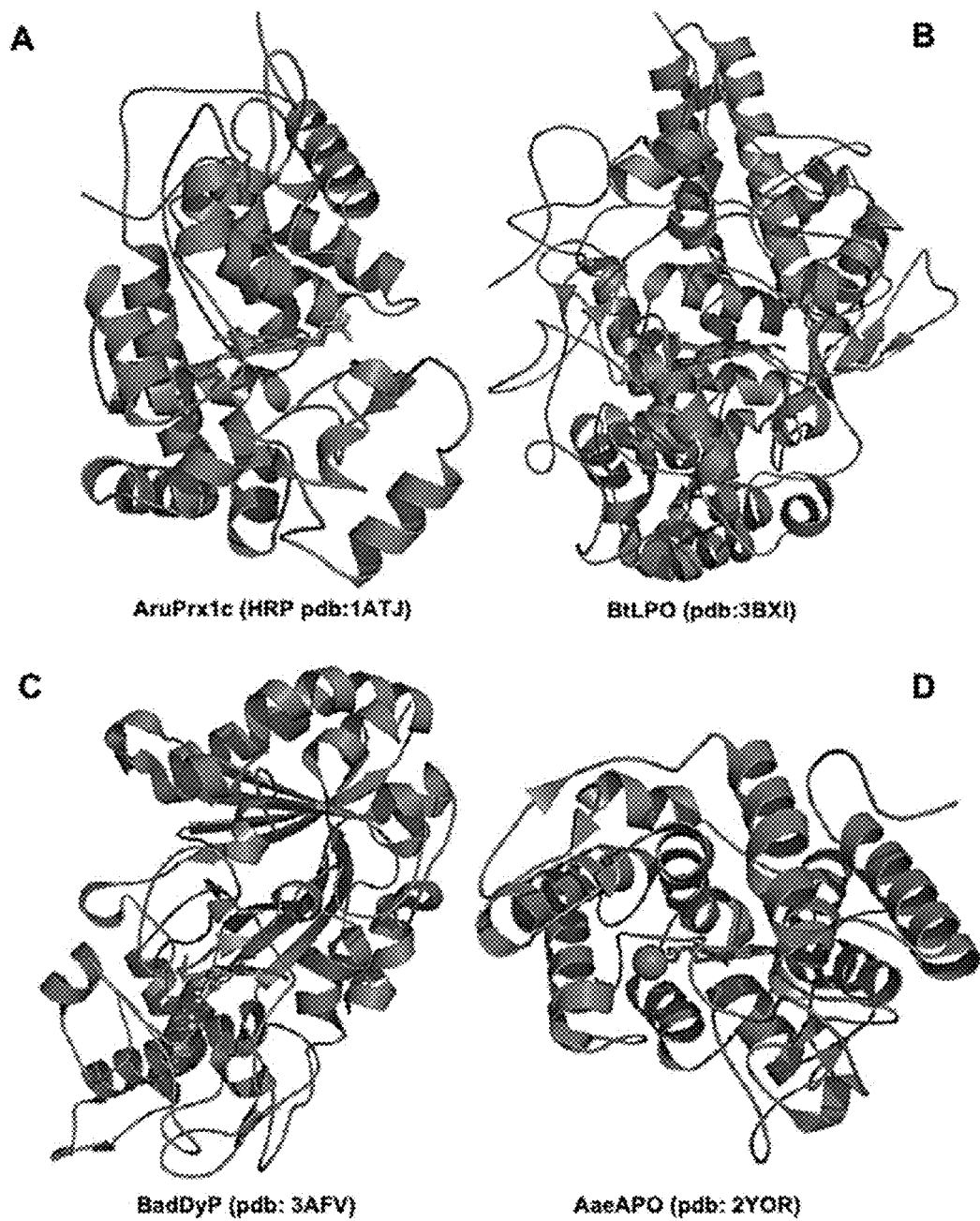
FIGS. 3A to 3D show structural folds for: (A) the peroxidase-catalase superfamily, (B) the peroxidase-cyclooxygenase superfamily, (C) the peroxidase-chlorite dismutase superfamily and (D) the peroxidase-peroxygenase superfamily.
Figure 3E:
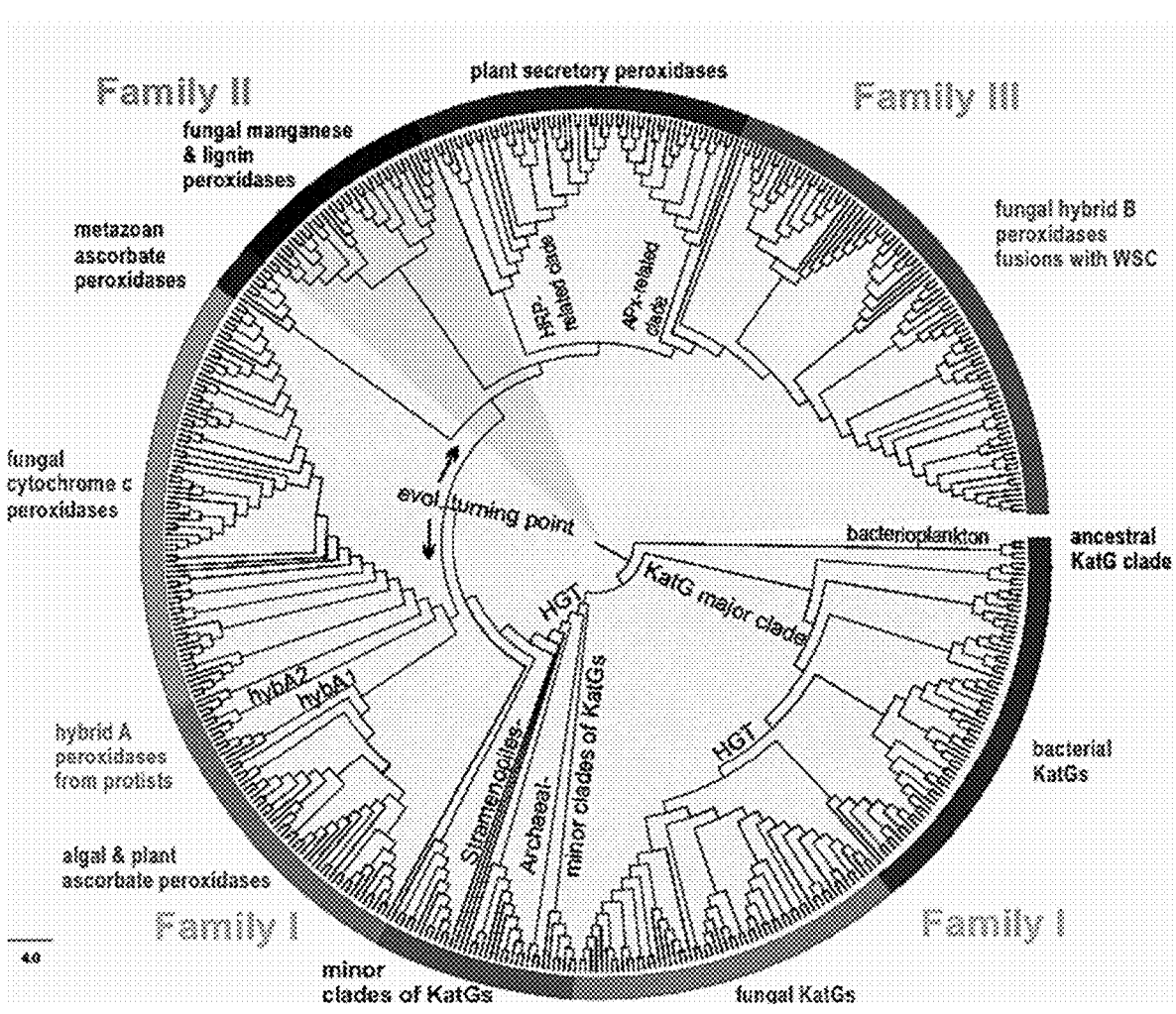
FIG. 3E shows a reconstructed phylogenetic tree of 500 members of the peroxidase-catalase superfamily. Adapted from M. Zamocky et al., Arch Biochem Biophys (2015) 574:108-119.

FIGS. 3A to 3D show representative structures, with prosthetic heme group for a typical member of (A) the peroxidase-catalase superfamily, (B) the peroxidase-cyclooxygenase superfamily, (C) the peroxidase-chlorite dismutase superfamily and (D) the peroxidase-peroxygenase superfamily. FIG. 3E shows a reconstructed phylogenetic tree of 500 members of the peroxidase-catalase superfamily. The evolutionary history was inferred by using the maximum likelihood method based on the Whelan & Goldman model implemented in MEGA 5 software. K. Tamura, D. Peterson et al., Mol. Biol. Evol. 28 (2011) 2731-2739.

DyP-type dye decolorizing peroxidases occur in fungi, bacteria, and archaea. They have several characteristics that distinguish them from all other peroxidases, including a wide substrate specificity, a lack of homology to most other peroxidases, and the ability to function well under much lower pH conditions compared with the other plant peroxidases. In terms of substrate specificity, DyP degrades the typical peroxidase substrates, and also degrades hydroxyl-free anthraquinone Crystal structures of DyP family members reveal two domains, each adopting a ferredoxin-like fold. Zubieta C et al., Proteins. 69 (2): 234-43. The proteins consist of an N-terminal domain and a C-terminal domain likely to be related by a duplication of an ancestral gene, as inferred from the conserved topology of the domains. The heme iron is typically penta-coordinated, with the protein contributing a conserved histidine ligand to the iron center. A conserved Asp is thought to as a proton donor and acceptor, taking the place of the catalytic histidine used by plant peroxidases, enabling it to be active at low pH.

FIGS. 3F and 3G show the predicted structure of DyP-peroxidase from Cellulomonas *bogoriensis*. DyP-peroxidase is typically a dimer with the active site buried in between the alpha helices and the beta sheets. Adapted from MH Habib et al., Molecules 2019, 24, 1208; doi:10.3390.

Ferritin Domain Proteins

Ferritin is a universal intracellular protein that stores iron and releases it in a controlled fashion. The protein is produced by almost all living organisms, including archaea, bacteria, algae, higher plants, and animals. It is the primary intracellular iron-storage protein in both prokaryotes and eukaryotes, keeping iron in a soluble and non-toxic form. In humans, it acts as a buffer against iron deficiency and iron overload. It is mostly a cytosolic protein, but small amounts are secreted into the serum where it functions as an iron carrier. Serum ferritin is also an indirect marker of the total amount of iron stored in the body; hence, serum ferritin is used as a diagnostic test for iron-deficiency anemia.

FIGS. 4A and 4B show the structure of Chaetopterus ferritin and its ion binding sites: (a) The crystal structure of a ferritin cage, with the 24-subunit ensemble spanning about 12.5 nm. Each subunit carries a ferroxidase center buried inside a four-helix bundle. (b) Three ferritin sub-units indicating the four-helix bundles delimiting a 3-fold channel and displaying metal ions at the location of the ion channel and the ferroxidase site (indicated with circles. c) The $Fe^{2+}/Fe^{3+}$ binding sites: A and B constitute the ferroxidase center, and site C is a ferrihydrite nucleation/gateway site. Adapted from P. Chen et al., Nature Sci Rep. 2020 Mar. 4; 10(1): 4033.

Indoleamine 2,3-Dioxgyenases and THAP4-Like Heme-Binding Proteins

Indoleamine 2,3-dioxgyenases are heme-containing enzymes that catalyze the conversion of tryptophan and other indole derivatives to kynurenines (Yuaha H J. et al. J Mol Evol. (2011) 72(2):160-168). Characterized members of this family of proteins perform various functions related to immune tolerance in mammals. These enzymes are also present in yeast, playing a role in the cellular response to telomere uncapping. Other members of the indoleamine 2,3-dioxygenase family include myoglobin from the red muscle of several mollusks. These unusual globins lack enzymatic activity but have kept the heme group (Suzuki T. et al. J Mol Biol.(1992) 228(2):698-700).

FIG. 4C shows the crystal structure of human indoleamine 2,3-dioxygenase 1 (IDO1) in complex with ferric heme and small molecule inhibitor MMG-0358. PDB accession no. 6R63, Roehrig, U. F. et al., 2019.

THAP4-like heme-binding proteins are widespread across all kingdoms of life and are characterized by including a beta-barrel domain. Enzymes from this family catalyze the conversion of peroxynitrite into nitrate. This reaction, scavenging peroxynitrite, protects free tyrosine against peroxynitrite-mediated nitration. Plant members of this family are nitrophorin-like heme-binding proteins that bind and are involved in the transport of nitric oxide, mediated by the heme group.

FIG. 4D shows the predicted structure of UPF0678 fatty acid-binding protein-like protein from *Panicum miliaceum*, which contains a THAP4-like heme-binding beta-barrel domain. UniProt Accession No. AOA3L6SSU6. FIG. 4E shows the predicted structure of another THAP4-like heme-binding beta-barrel domain-containing protein from *Oryza punctata* (red rice): UniProt. accession no. A0A0E0JMF. The heme binding site generally is within the barrel domain, in which case the user has the option of expressing this subcategory of PX90 proteins without the hydrophilic tail of the protein.

Altered Forms of PX90 Proteins

Some subcategories of PX90 proteins, such as DyP type peroxidases, indoleamine 2,3-dioxgyenases, and THAP4-like heme-binding proteins, include members in which the naturally occurring form and/or a splice variant thereof has enzymatic activity. The enzymatic activity may be beneficial to the consumer (for example, improving digestion), or it may be harmless to the consumer. In either case, the PX90 protein may be used in its naturally occurring form.

In some instances, the naturally occurring enzyme activity may be deemed unfavorable for human consumption, in which case the user has the option of altering the PX90 protein before incorporation into a nutritional supplement or food ingredient. The altered form can be designed empirically, for example, by truncating the protein from either the N- or the C-terminus while testing both heme binding and enzymatic activity, until a limit fragment is obtained from which enzymatic activity has been deleted, while the heme binding activity has been retained. Alternatively, the altered form may be rationally designed with reference to the known three-dimensional structure of the protein. Knowing the locations of the heme binding site and the enzyme catalytic site, amino acid changes are made to the sequence in the form of substitutions, additions, or deletions that remove residues essential to the enzyme catalytic site, or cause refolding of the protein so that the enzyme substrate or an enzyme cofactor does not bind.

To avoid altered forms that have an increased potential for immunogenicity or allergenicity, candidate alterations can be filtered using predictive computer algorithms. For example, allergenicity can be predicted in the manner of L. Zhang et al., Bioinformatics 2012, 28:2178-2179; L. Wang et al., Foods 2021, 10:809, doi.org/10.3390; and S. Saha et al., Nucl. Acids Res. 2006, 34, doi:10.1093. Immunogenicity can be predicted in terms of MHG binding motifs and T and B cell epitopes algorithmically in the manner of N. Doneva et al., Symmetry 2021:13, 388. Toxicity can be predicted in the manner of S. S. Negi et al., Sci. Reports 2017:7, 13957-1; and Y. Jin et al., Food Chem. Toxicol. 2017; 109:81-89. Candidate alterations that are not disqualified by the screening algorithms are then expressed and tested empirically for safety and suitability.

Manufacture and Purification of Protein as Food Ingredients

Generally, proteins can be recombinantly produced by inserting a transgene encoding its amino acid sequence into a suitable expression host. The host cell is thereby genetically modified to integrate DNA or carry plasmids designed to express the protein of interest constitutively or via induction. Suitable organisms used for recombinant expression of candidate proteins are listed in TABLE 3. Host organism selection takes into consideration the ability for the host to express soluble protein in high quantities with the posttranslational modifications (such as addition of carbohydrates and/or interchain crosslinking) that may affect protein function.

TABLE 3

| Recombinant expression systems for candidate proteins | |
| --- | --- |
| Organism | Strain |
| animal | *Drosophila* S2 |
| animal | SF9 |
| animal | SF21 |
| animal | CHO |
| yeast | *Pichia pastoris* (*Komagataella phaffi*) |
| yeast | *Saccharomyces cerevisiae* |
| filamentous fungi | *Aspergilllus* |
| filamentous fungi | *Trichoderma reesi* |
| filamentous fungi | *Neurospora crassa* |
| bacteria | *E. coli* |
| plant | *Nicotiana benthamiana* |
| plant | *Solanum lycopersicum* |
| algae | *Chlamydomonas reinhardtii* |
| cell free | plant extract |
| cell free | bacteria extract |
| cell free | yeast extract |

Eukaryotic expression systems have the advantage of performing post-translational processing of protein candidates in a manner akin to what may be used naturally or for industrial production, such as glycosylation and interchain crosslinking. Prokaryotic expression systems have the advantage of being easy to implement and obtain high yield. It is possible to use several systems during development: for example, expression in *E. coli* for performing screening assays; and expression in eukaryotes for later stage development and testing. Some expression systems such as yeast are suitable for use in both stages.

Common purification methods include centrifugation, filtration, affinity chromatography, ion exchange chromatography, size exclusion chromatography, hydrophobic interaction chromatography, affinity capture, isoelectric precipitation, liquid-liquid phase separation (LLPS), lyophilization, and dialysis. One of these methods may be used as a single step or combined with other methods as needed to achieve a desired level of purity. Once achieved, the protein is processed by standard methods into a final condition that is compatible with characterization methods. For example, some assay methods may require powdered protein, while other characterization methods may require proteins in aqueous solution. For general principles, the reader is referred to the following texts: *Protein Purification*, 2nd Ed., P. Bonner, 2018; and *High-Throughput Protein Production and Purification*, R. Vincentelli ed., 2019. To facilitate protein purification for the purpose of initial testing of PX90 protein candidates, recombinant protein can be expressed with an exclusive tag for affinity binding. The tag can be any feature added to the protein during expression that can be used as a handle for affinity purification using a conjugate binding partner. Examples include amino acid sequences added internally or to either end of the naturally occurring protein sequence, and carbohydrates. After the tagged protein is immobilized on an affinity surface, fermentation byproducts can be washed away. Depending on the tag used, the purified target protein can then be eluted from the resin using competitive binding or a condition change, such as pH.

Biosynthesis of Heme

An additional consideration in the preparation of PX90 proteins is to use as an expression host a cell that has the capacity to make a heme or other porphyrin that the PX90 protein will carry, and supply an iron atom to be bound by the heme. A prokaryotic or eukaryotic organism is selected that has porphyrin assembling enzymes. Alternatively, for some proteins that can bind heme after folding, the heme binding amino acid sequence can be prepared separately, and then combined with a biosynthesized host at a later time.

Iron-binding porphyrins (specifically, tetrapyrroles) include hemes, chlorophylls, and cobalamin. Heme serves as a prosthetic group of many proteins involved in respiration, photosynthesis, and the metabolism and transport of oxygen. Enzymes such as catalases, peroxidases, or cytochromes P450 rely on heme as essential cofactors.

The enzymes that participate in the biosynthetic pathways for heme in living cells include the following:

5-aminolevulinate-synthase (ALAS);
glutamyl-tRNA-reductase-(GluTR);
glutamate-1-semialdehyde-2;
1-aminomutase-(GSAM);
orphobilinogen-synthase-(PBGS);
porphobilinogen-deaminase (PBGD);
uroporphyrinogen-III-synthase (UROS);
uroporphyrinogen-III-decarboxylase (UROD);
oxygen-dependent-coproporphyrinogen-III-oxidase (CPO);
coproporphyrinogen-III-dehydrogenase (CPDH) (also-known-as-oxygen-independent-coproporphyrinogen-III-oxidase);

oxygen-dependent-protoporphyrinogen-IX-oxidase (PPO); and
ferrochelatase (FC).

These enzymes, their structure, and their role in heme biosynthesis are reviewed by G Layer et al. (2010) Protein Sci. 19:1137-1161.

Host cells selected by the user for expression of heme binding proteins may also contain one or a plurality of transgene for expressions of one or more of these heme producing enzymes, to facilitate production of heme-loaded proteins. Culture medium will typically contain an effective amount of iron for loading into the heme.

Production and Purification of PX90 Proteins

PX90 proteins can be prepared for initial testing using standard bacterial or eukaryotic expression and purification methods, for example, using a pET28a (+) vector with expression induced using a lactose inducible promoter system. Plasmids were constructed to include a C-terminal 6X-HIS tag for purposes of detection as well as purification.

To obtain protein for physicochemical characterization, strains containing an encoding sequence for a desired PX90 protein are grown at 30° C. at a scale of 2 mL to 10 µL using 24-deep well plates or shake flasks, depending on volume. Standard Luria Broth (LB) media with IPTG induction or commercially available auto-induction media (such as MagicMedia™) causes overexpression of the PX90 protein. Cells are harvested after approximately 48 h via centrifugation. Cells are then suspended 50 mM phosphate buffer, 500 mM sodium chloride, pH 7.5 for cell lysis. Cells are lysed using different methods depending on the scale using standard protocols for BugBuster®, sonication, or pressure homogenization. Lysate is then centrifuged to remove cellular debris.

Solubilized protein is collected and clarified using filtration with a 0.45 µM cutoff. Protein is purified using immobilized metal affinity chromatography and separated from contaminants by collecting fractionated eluate using an elution gradient 0 to 250 mM imidazole over 8 column volumes. Fractions containing the PX90 protein are identified by SDS-PAGE analysis, and pooled together. Protein volume is concentrated approximately 10-fold using tangential flow filtration cassettes with a molecular weight cutoff of 10 kDa. Salt is then removed from the PX90 protein by exchanging buffer to 18.2 megohm ionic strength water at a ratio of 1:40 for four successive exchanges using a method such as dialysis. The protein is dried by lyophilization for subsequent characterization and use.

Production of PX90 proteins can be scaled up for commercial manufacture for use as a food ingredient using other synthesis and purification protocols. Production methods may include changing the recombinant expression host to any one of the generally regarded as safe (GRAS) hosts, such as *Pichia* or *Aspergillus*. Protein can be produced via fermentation in a bioreactor, which can be sized for production of one to 10,000 liters. When used as a food ingredient, removal of artificial affinity tags is desirable, whereupon the protein is purified by other means. If protein is soluble and intracellular, cells must be lysed and cell debris must be removed, which can be done via centrifugation and filtration.

PX900 protein can then be recovered via standard separation techniques such as fractionation, filtration, or a combination of separation techniques used in tandem. If protein is secreted from the host cell, then cell lysis may be omitted. Biochemical properties of the protein may be used to guide selection of such steps. For example, a molecular weight of 60 kDa can be used to select filtration methods with a molecular weight cutoff smaller than the protein, such that the PX90 protein remains in the retentate while filtration with a molecular weight cutoff greater than the protein such that the protein passes to the permeate. The isoelectric point of protein can be used to guide pH at which the protein may become unstable and precipitate from solution. Such precipitation steps can be used to fractionate the PX90 protein from cellular debris and off-target proteins.

General Principles of Protein Characterization

Purified PX90 protein candidates can be tested for various physicochemical properties, as listed in TABLE 4.

TABLE 4

| Assessing biochemical properties | |
| --- | --- |
| Biochemical property | Assays |
| oligomerization state | size exclusion chromatography, native PAGE |
| concentration | Bradford ™, Pierce 660 ™, absorbance spectroscopy |
| purity | amino acid analysis, proximate analysis, gel electrophoresis, capillary electrophoresis |
| buffering capacity | titration |
| pH | indicator strips, pH probe |
| enzyme activity | colorimetric assays, fluorometric assays, absorbance spectroscopy |
| molecular weight | gel electrophoresis, capillary electrophoresis |
| degradation | gel electrophoresis, amino acid analysis |
| conductivity | conductivity probe |
| % random coil | circular dichroism |
| % alpha helix | circular dichroism |
| % beta sheet | circular dichroism |
| zeta potential | phase analysis light scattering |
| solubility | fluorometric assays, colorimetric assays |
| aggregation | dynamic light scattering, centrifugation, size exclusion chromatography, fluorescence-based assays |
| particle size distribution | dynamic light scattering |
| melting temperature (tm) | differential scanning calorimetry, thermal shift assay |
| heat capacity | differential scanning calorimetry, thermal shift assay |
| surface hydrophobicity | fluorometric assay |
| % thiols | fluorometric assay |
| sulfur content | fluorometric assay |
| density biophysical | calculated |
| glycosylation content | mass-spectroscopy |

Measuring Heme Binding or Heme Content

As a matter of quality control, the user will likely want to test the expression product for presence of heme, and for iron content. Affinity determination can be made by setting up a binding reaction of the candidate protein and heme, measuring the reaction kinetics.

Figure 5A:
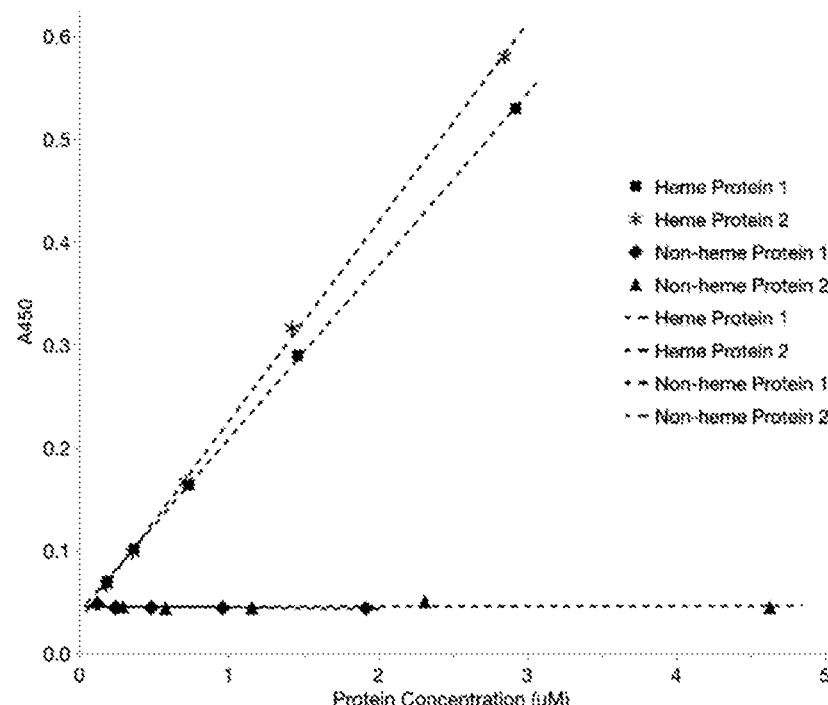
FIG. 5A shows results of an assay to quantify heme content of recombinantly expressed protein samples, using the 1-step Turbo-TMB reagent from ThermoFisher.

FIG. 5A provides an illustration of an assay method used to measure heme binding activity of recombinantly expressed proteins. The assay is performed using 1-step Turbo-TMB reagent (ThermoFisher) according to manufacturer's directions. The reagent contains 3,3',5,5'-tetramethylbenzidine (TMB) and a stabilized hydrogen peroxide and reacts with free or protein-bound heme groups via oxidation of TMB by the ferryl iron-oxo heme intermediate, resulting in a colorimetric output. The reaction is highly specific to heme-containing purified or crude biological sample preparations. Sample processing begins by mixing of 20 µL biological sample with 80 µL of 1-step Turbo-TMB reagent in a flat-bottom, clear assay plate for UV-visible absorbance measurements. Plates are incubated at room temperature for 30 min, and the reaction is quenched using 100 µL of 1 M hydrochloric acid solution. The absorbance of the quenched reaction samples is read at 450 nm. The amount of reaction product is proportional to the heme content of the expressed protein.

Figure 5B:
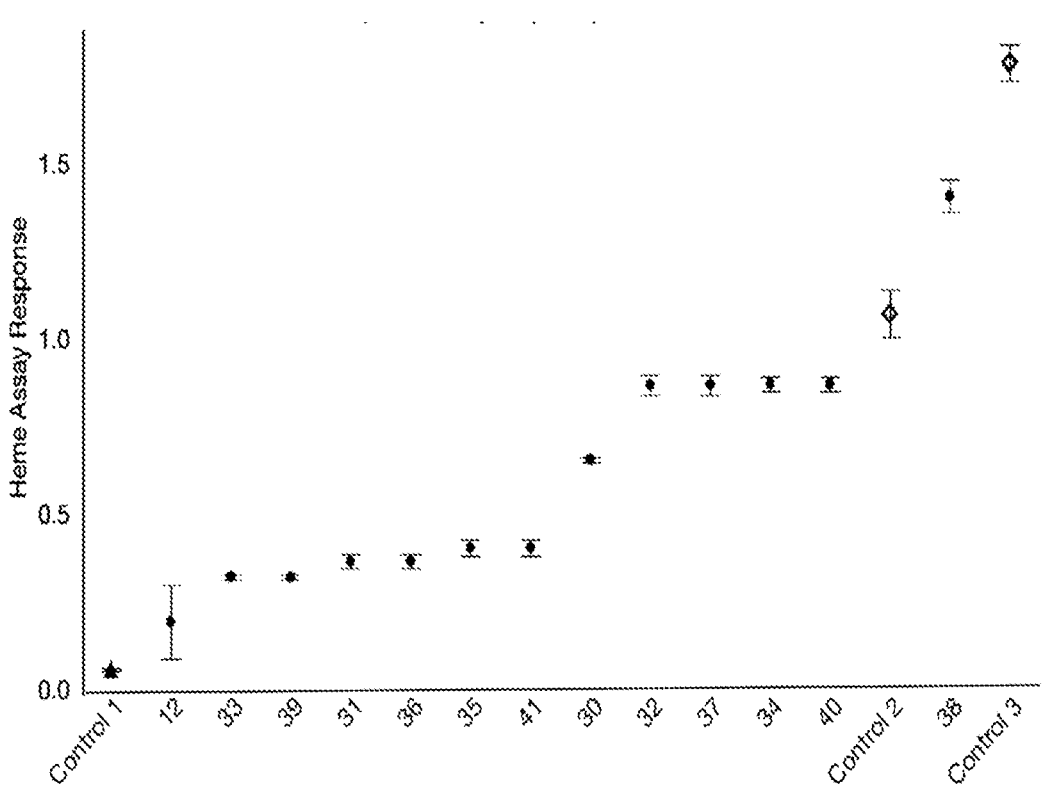
FIG. 5B provides heme binding data for the candidates listed in TABLE 1B. The mean heme assay response for five assay replicates is shown, with error bars representing standard deviation.

FIG. 5B provides heme binding data for the candidates listed in TABLE 1B. The mean heme assay response for five assay replicates is shown, with error bars representing standard deviation. Negative Control 1=mCherry (non-heme protein with validated expression). Positive Control 2=soy leghemoglobin, Positive Control 3=bovine myoglobin. Positive heme expression is determined wherever the heme assay signal on this scale was 0.1.

Assessing Other Functional and Physicochemical Properties

In surveying and testing other members of the PX90 protein family, the user may also wish to determine whether a candidate has other desirable functions or properties, thereby increasing the favorability rating of the candidate— and whether it has one or more undesirable functions or properties, thereby decreasing the favorability rating of the candidate or removing it from contention. By way of illustration, desirable properties may include one or more of the following: ease of expression, ease of purification, stability when stored, mixability, and one or more desirable flavors or sensory properties. Undesirable properties may include one or more of the following: allergenicity or immunogenicity, incompatibility with other food ingredients, an adverse physiological effect, and an undesirable flavor.

Computer algorithms are available to predict some of these properties. For example, allergenicity can be predicted in the manner of L. Zhang et al., Bioinformatics 2012, 28:2178-2179; L. Wang et al., Foods 2021, 10:809, doi.org/ 10.3390; and S. Saha et al., Nucl. Acids Res. 2006, 34, doi:10.1093. Immunogenicity can be predicted in terms of MHG binding motifs and T and B cell epitopes algorithmically in the manner of N. Doneva et al., Symmetry 2021:13, 388. Toxicity can be predicted in the manner of S. S. Negi et al., Sci. Reports 2017:7, 13957-1; and Y. Jin et al., Food Chem. Toxicol. 2017; 109:81-89. Aspects of flavor can be predicted in the manner of P. Keska et al., J. Sensory Studies 2017:e12301; F. Fritz et al., Nucleic Acids Res. 2021 Jul. 2; 49(W1):W679-W684' and S. Ployon et al., Food Chem. 2018 Jul. 1; 253:79-87. Other properties are assessed by laboratory testing.

General Considerations of Dietary Iron Content and Supplementation

Heme binding proteins put forth in this disclosure can be used as a component of a commercial food product, or as part of a concentrated nutritional supplement.

Intake recommendations for iron and other nutrients have been established as the Dietary Reference Intakes (DRIs) developed by the Food and Nutrition Board (FNB) at the Institute of Medicine (IOM) of the National Academies. The recommended daily allowances for elemental iron are shown in TABLE 5. RDAs increase to 27 mg during pregnancy, and to 9-10 mg during lactation.

TABLE 5

| Recommended daily allowances (RDA) of iron | | |
|---|---|---|
| Age | Male | Female |
| 7 to 12 months | 11 mg | 11 mg |
| 1 to 3 years | 7 mg | 7 mg |
| 4 to 8 years | 10 mg | 10 mg |
| 9 to 13 years | 8 mg | 8 mg |
| 14 to 18 years | 11 mg | 15 mg |
| 19 to 50 years | 8 mg | 18 mg |
| over 51 years | 8 mg | 8 mg |

According to the National Institutes of Health (Office of Dietary Supplements), most of the 3 to 4 grams of elemental iron in adults is in the form of hemoglobin in red blood cells. Much of the remaining iron is stored in the form of ferritin or hemosiderin (a degradation product of ferritin) in the liver, spleen, and bone marrow or is located in myoglobin in muscle tissue Transferrin is the main protein in blood that binds to iron and transports it throughout the body. Humans typically lose small amounts of iron in urine, feces, the gastrointestinal tract, and skin. Losses are greater in menstruating women because of blood loss. Hepcidin, a circulating peptide hormone, is the key regulator of both iron absorption and the distribution of iron throughout the body, including in plasma.

Some groups of consumers are more likely to have inadequate intakes of iron. During pregnancy, plasma volume and red cell mass expand due to dramatic increases in maternal red blood cell production. As a result of this expansion and to meet the needs of the fetus and placenta, the amount of iron that women need increases during pregnancy.

Infants (especially those born preterm or with low birthweight or whose mothers have iron deficiency) are themselves at risk of iron deficiency because of their high iron requirements due to rapid growth. Full-term infants have a risk of becoming iron deficient at 6 to 9 months of age, unless they obtain adequate amounts of solid foods that are rich in bioavailable iron or iron-fortified formula. Women of reproductive age who have menorrhagia are also at increased risk of iron deficiency. Frequent blood donors also have an increased risk of iron deficiency: in fact, about 30% of regular blood donors develop iron deficiency.

Trained athletes can experience low levels of blood hemoglobin (below 13 to 14 g/100 mL in men or 12 g/100 mL in women), plus low hematocrit and low ferritin levels—known as sports anemia. Low iron levels may be due to mechanical hemolysis, intestinal bleeding, hematuria, sweating, low iron intake, poor intestinal absorption, and combinations thereof. The resulting decrease in oxygen transport by the circulation and muscle activity impairs athletic performance.

Iron deficiency and its sequelae can be secondary to other disease conditions. Up to 60% of patients with colon cancer have iron deficiency at diagnosis, probably due to chronic blood loss. The prevalence of iron deficiency in patients with other types of cancer ranges from 29% to 46%. The main causes of iron deficiency in people with cancer are anemia of chronic disease, and chemotherapy-induced anemia. People with certain gastrointestinal disorders (such as celiac disease, ulcerative colitis, and Crohn's disease) or who have undergone certain gastrointestinal surgical procedures (such as gastrectomy or intestinal resection) have an increased risk of iron deficiency because their disorder or surgery requires dietary restrictions or results in iron malabsorption or blood loss in the gastrointestinal tract. Approximately 60% of patients with chronic heart failure also have iron deficiency, which is attributed to poor nutrition, malabsorption, defective mobilization of iron stores, cardiac cachexia, and use of aspirin and other oral anticoagulants.

Iron deficiency progresses from depletion of iron stores (mild iron deficiency) to iron-deficiency erythropoiesis, and finally to iron deficiency anemia (IDA). With iron-deficiency erythropoiesis (also known as marginal iron deficiency), iron stores are depleted and transferrin saturation declines, but hemoglobin levels are usually within the normal range. IDA is characterized by low hemoglobin concentrations, and decreases in hematocrit (the proportion of red blood cells in blood by volume) and mean corpuscular volume (a measure of erythrocyte size).

The richest sources of heme iron in a normal diet include lean meat and seafood. Dietary sources of nonheme iron include nuts, beans, vegetables, and fortified grain products. In the United States, about half of dietary iron comes from bread, cereal, and other grain products. Breast milk contains highly bioavailable iron but in amounts that are not sufficient to meet the needs of infants older than 4 to 6 months. In the United States, Canada, and many other countries, wheat and other flours are fortified with iron. Infant formulas are fortified with 12 mg iron per liter.

The 2020-2025 *Dietary Guidelines for Americans* recommends that iron requirements be met primarily by eating a healthy diet. However, in some cases, fortified foods and dietary supplements are useful when it is not possible otherwise to meet needs for one or more nutrients.

Depending on the consumer's condition and diet, the amount of iron in supplements must be titrated appropriately to avoid iron overload. Supplements containing 25 mg iron or more can reduce zinc absorption and plasma zinc concentrations. High-dose iron supplements can also cause gastrointestinal effects, including gastric upset, constipation, nausea, abdominal pain, vomiting, and diarrhea. Consumers having hemochromatosis disease caused by a mutation in the hemochromatosis gene) are especially at risk of an excessive buildup of iron in the body. The FDA requires that oral supplements containing more than 30 mg elemental iron per dose be sold in single-dose packaging with strong warning labels. The FNB has established that the upper intake levels of iron for most consumers is 40 mg per day.

Use of a PX90 Protein as a Dietary Supplement

Heme iron has higher bioavailability than nonheme iron, and other dietary components have less effect on the bioavailability of heme than nonheme iron. Murray-Kolbe L E et al., in: Coates P M, et al., eds. *Encyclopedia of Dietary Supplements*. 2nd ed., 2010; Hurrell R, Egli et al., Am J Clin Nutr 2010; 91:1461S-7S. For this reason, the PX90 proteins of this disclosure are well suited as a basis for nutritional iron supplements.

Consumers that will benefit from supplementation include those with insufficient dietary iron, or who have signs or symptoms of anemia, low hematocrit, low red blood cell count, low reticulocyte count, iron deficiency, or decreased mean corpuscular volume. Supplements containing mostly iron will have 5 to 50 mg, more typically 10 to 25 mg of elemental iron, in the form of a PX90 protein. The dose range may be adjusted downwards to take into account the higher bioavailability of heme iron.

The PX90 protein can be part of a combined supplement that may also contain the recommended daily intake of one or more vitamins such as biotin, folate, Vitamin A palmitate, thiamin, riboflavin, niacin, pantothenic acid, pyridoxine, cobalamin, ascorbic acid, cholecalciferol, and Vitamin K; and/or one or more minerals such as calcium, chromium, copper, fluorine, iodine, iron, magnesium, manganese, molybdenum, phosphorus, selenium, and zinc. The formulation will typically also contain one or more pharmaceutically compatible excipients and/or other proteins of at least 2, 5, or 10% by weight. It can be supplied in the form of capsules or tablets with each unit dose being the recommended daily intake or supplementation of each of the combined nutrients.

The PX90 proteins of this disclosure can also be added to processed food products at a concentration that will supply a part of the consumer's dietary needs for iron. The objective may be to provide an increased amount of iron compared with what naturally occurs in the product. Alternatively, the objective may be to simply match the typical iron content of a particular foodstuff when standard ingredients are replaced with synthetic ingredients or recombinant protein that have less iron: for example, when myoglobin containing muscle cells in meat or replaced with a plant protein, especially when made in recombinant culture.

Generally, the content of PX90 protein in a food or dietary supplement will be 0.05% to 20% by weight, more typically 0.2% to 5% by weight. The heme in heme binding proteins may affect the flavor of the food product. This may be attractive to consumers in certain food products, including but not limited to meat substitutes. It may be less attractive in foods such as dairy products and desserts, in which case the amount of PX90 protein in the food product can be adjusted downwards, and/or the taste can be masked with other ingredients.

Use of a PX90 Protein in Food to Affect Taste and Color of Food Products

There is an enormous interest in developing plant-based meat substitutes. Consumers tend to prefer meat substitutes that have a taste and texture that mimics the animal-based products that they are replacing. There has been considerable research on what makes meat taste and smell like meat. The effect is a combination of a number of different chemicals present in the food and created during preparation or cooking that affect the olfactory (smell) and gustatory (taste) receptors in a complex fashion.

Meat-like flavor or aroma can be created in food products in part by release of volatile compounds that have a meat associated aroma: for example, 2-methyl-furan, bis(2-methyl-3-furyl)disulfide, 2-pentyl-furan, 3,3'-dithiobis-2-methyl-furan, 2,5-dimethyl-pyrazine, 2-methyl-3-furanthiol, dihydro-3-(2H)-thiophenone, 5-methyl-2-thiophenecarbox-aldehyde, 3-methyl-2-thiophenecarboxaldehyde, 2-methyl-thiazole, dimethyl sulfide, decanal, 5-ethyldihydro-2(3H)-furanone, dihydro-5-pentyl-2(3H)-furanone, 2-octanone, 3,5-octadien-2-one, p-Cresol, and hexanoic acid.

Depending on context and intended use, other components that may contribute to a meat-like flavor or aroma are sugars, other carbohydrates, and sulfur-containing compound that may or may not be part of a protein in the food. In meat substitutes, the sugar may be selected from glucose, ribose, fructose, lactose, xylose, arabinose, glucose-6-phosphate, maltose, and galactose, and mixtures of two or more thereof. The sulfur-containing compound may be selected from cysteine, cystine, selenocysteine, thiamine, methionine, and mixtures of two or more thereof.

Preparation and features of some meat substitutes and flavorings are outlined in U.S. Pat. Nos. 3,815,823; 9,700, 067; 10,863,761; 10,798,958; and 11,013,250; and in EP 3952661 A1.

Meat substitutes and flavoring products can be made from plant components or other ingredients by combining about 60% (wt/wt) muscle replica (made up, for example, of 62% (wt/wt) dark muscle replica and 38% (wt/wt) white muscle replica), about 30% (wt/wt) fat tissue replica, and about 5% (wt/wt) connective tissue replica. U.S. Pat. No. 10,863,761. Muscle tissue replica can be made by combining a PX90 heme binding protein (12 mg/mL) with about an equal volume of plant protein (150 mg/mL) in the presence of a crosslinking agent such as transglutaminase (about 10% wt/vol). Fat tissue replica can be made from moong seed storage 8S globulin or pea globulin by combining with an oil such as soy or rice bran oil in the presence of transglutaminase by heating at ~95° C. for 5 min and then cooling. Fat tissue replica typically forms an opaque gel of off-white color, smooth uniform texture, with no visible discernible liquid that was not incorporated into the gel. Connective tissue replica can be prepared as a combination of plant proteins or structural equivalents that mimic collagen or fascia like fibers, or a combination of the two.

The presence of an iron-containing porphyrin in food products will also affect color: typically visible as a shade of red or brown. For meat substitutes, the balance of PX90 proteins and other components ideally creates a pink or red color before cooking, which progresses to a brownish color after cooking. If coloring of this type is not desired in a food product (such as an ice cream), the user may adapt the PX90 protein by using a lower concentration, or by including other coloring agents in the food product that will supersede the color produced by the PX90 protein.

Using a PX90 Encoding Sequence as a Transgene for Food Production

For food products made from plants or in tissue culture, rather than adding PX90 into the food products at the formulation stage, the user may biosynthesize the PX90 protein concurrently with the biosynthesis of other components of the food product. For example, if a food being developed will have a PX90 protein (say, at 0.5 to 5% by weight) and a gelation protein (say, at 1 or 2 to 10% by weight), the two recombinant proteins can be produced together in a single host: for example, a cultured cell such as yeast, or a transgenic plant such as wheat or corn.

To accomplish this, a chosen host cell is transfected with a transgene that includes a nucleic acid encoding sequence for the chosen PX90 protein, and one or more additional transgenes that include a nucleic acid encoding sequences for additional protein components that will be included in a food product. The host cell or plant is cultured or grown in a manner that will produce both proteins, which are already combined so as not to require the same extent of purification or refinement. The ratio of production of the two or more proteins can be adjusted during the culturing or growing of the host cell or plant by placing at least one of the encoding sequences under control of an inducible promoter—titrating the availability of the inducing agent to achieve the desired ratio of protein production.

Examples of Food Products Incorporating One or More PX90 Proteins

The reader may incorporate PX90 proteins into food products at a mass ratio that is appropriate for the degree of nutritional supplementation or flavor enhancement that is desired. This will depend on the other ingredients in the product, whether the product will be heated or otherwise processed by the consumer, and the particular PX90 protein chosen.

In general, any concentration of between 0.10% and 20% wt/wt of dry ingredients may be used. A range of 0.2% or 0.5% to 5% or 10% is more typical.

The products may be made with traditional animal fats and/or plant-based oil. Alternatively or in addition, they may be made with an oleogel (an oil dispersed in a protein microstructure) made using a plant-based protein, as described in U.S. provisional patent application 63/451,645, filed Mar. 13, 2023.

Plant-Based Patties and Meatballs

PX90 proteins can be used to improve nutrition and taste of meat substitutes, as illustrated in the following recipes.

TABLE 6A

Ingredients for plant-based beef-like products

|  | Quantity (g) | Quantity (% wt/wt) |
|---|---|---|
| Water | 240 | 46.5% |
| Texturized vegetable protein (TVP) | 100 | 19.4% |
| Heme containing PX90 protein | 1.5 | 1% |
| Binder such as methylcellulose | 6 | 1 to 7% |
| Beet powder (color agent) | 3 | 0.6% |
| Gelling agent such as fava bean protein | 30 | 0 to 6% |
| Garlic powder | 0.9 | 0.2% |
| Nutritional yeast | 6 | 1.2% |
| Dried onion | 0.8 | 0.2% |
| Cocoa powder | 2 | 0.4% |
| Ground thyme | 0.4 | 0.1% |
| White pepper | 1 | 0.2% |
| Malt vinegar powder | 8 | 1.5% |
| Liquid aminos (soy sauce) | 15 | 2.9% |
| Liquid smoke | 1.2 | 0.2% |
| Coconut oil or oleogel | 100 | 19.4% |

Meat-Like Patties can be Prepared as Follows;
1. Weigh all dry ingredients
2. Weigh liquid ingredients separately
3. Mix the liquid ingredients with the dry ingredients to form a dough
4. Let the dough hydrate for 20 min at room temperature
5. Make beads of coconut oil: by freezing the coconut oil followed by scraping it with fork, cheese grater or in blender
6. Add half of the coconut oil beads and mix
7. Add the second half of coconut oil beads and gently fold to give a marbled look
8. Plant-based patties cooking procedure:
9. Weigh dough and divide into balls of 50 g
10. Shape them into patties using a patty press maker (2.5" diameter, measure diameter and weigh the patty again) or shape them into balls for meatballs (50 g each)
11. Cook in non-stick pan (at 150° C. for 5 min per side, flip 3 times or until internal temperature reaches 75° C.)

Plant-Based Meat-Like Meatballs can be Made as Follows:
1. Preheat oven 400° F.
2. Make balls by hand (25 g each) and place on a baking sheet (use parchment paper)
3. Bake for 20-25 min. Turn meatballs halfway into the timer Plant-Based Sausages To make sausages, the following items are combined and packed into a vegetarian casing:

TABLE 6B

Ingredients for plant-based sausages

|  | Quantity (% wt/wt) |
|---|---|
| Water | 37.7% |
| Texturized Vegetable Protein (TVP) | 15.7% |
| Heme containing PX90 protein | 1% |
| Sausage binder (Solution of methylcellulose; 3-8% wt/wt solution in water) | 16.6% |
| Beet powder | 0.5% |
| Fava bean protein | 4.7% |
| Garlic powder | 0.9% |
| Nutritional yeast | 0.9% |
| Dried onion | 0.1% |
| Cocoa powder | 0.3% |
| Ground thyme | 0.1% |
| white pepper | 0.2% |
| Malt vinegar powder | 1.3% |
| Salt | 1.1% |
| Black pepper | 0.2% |
| Sugar | 0.2% |
| Extra seasoning mix | 0.9 |
| Soy sauce | 2.4% |
| Liquid smoke | 0.2% |
| Coconut oil or oleogel | 15.7% |

Preparation is as Follows:
1. Weigh all ingredients
2. Weigh all dry ingredients
3. Make the sausage binder by mixing a gelation causing protein with water until completely dissolved
4. Weigh liquid ingredients separately
5. Mix the liquid ingredients with the dry ingredients and the binder to form a dough in the standing mixer at medium speed
6. Let the dough hydrate for 20 mi at room temperature
7. Place the sausage filler attachment in the standing mixer with the vegetarian casing
8. Fill the vegetarian casings with the dough and refrigerate or cook in a pan.

Plant-Based Chicken-Like Nuggets

TABLE 6C

Ingredients for plant-based chicken nuggets

|  | Quantity (% wt/wt) |
|---|---|
| Water | 57 |
| Potato starch | 13-18 |
| Texturized vegetable protein | 17 |
| Heme containing PX90 protein | 1 |
| Vegetable oil | 3.5 |
| Baking powder | 2.5 |
| Methylcellulose | 1~5 |
| Salt | 0.3 |
| Calcium chloride* | 0.2 |

Baking powder and calcium chloride are added to enhance protein water binding capacity and generate the formation of air cells in the dough.

Preparation is as Follows:
1. Weigh ingredients
2. Prepare protein emulsion/dough. By mixing all ingredients in a food processor for 5 min at low speed
3. Mold and shape plant-based nuggets batter
4. Steam the molded batter (100° C. for 14 min)
5. Coat with batter (flour and water 1:2) and deep-fry for 1.5 min
6. Freeze at −20° C.
7. Bake at 220° C. for 15 min Plant-Based Ice Cream

TABLE 6D

| Ingredients for ice cream | |
| --- | --- |
| | Quantity (% wt/wt) |
| Water | 55 to 65 |
| Soymilk powder or pea protein concentrate | 4.4 |
| Texturized vegetable protein | 8 |
| Heme containing PX90 protein | 0.2 |
| Safflower oil, vegetable oil, or oleogel | 8 |
| Sweetener (sugar, syrup) | 22.6 |
| Tapioca solids | 2 to 5 |
| Stabilizers | 0.2 to 3 |

Protein:fat interaction affects characteristics such as melting rate, stability (mix separation), textural qualities, overrun, and viscosity.

Preparation is as Follows:
1. Weigh ingredients
2. Mix soy milk or pea protein powders with water in a saucepan (at 45 to 50° C.) while continuously stirring.
3. Incorporate the rest of the ingredients to the warm mixture while constantly stirring
4. Homogenize ingredients at 15,000 rpm for 3 min.
5. Age the mixture (at 5° C. for up to 24 h)
6. Freeze the mixture while incorporating air (using an ice cream maker) for 20 min Plant-Based Flan or Custard

TABLE 6E

| Ingredients for flan or custard | |
| --- | --- |
| | Quantity (% wt/wt) |
| Full fat coconut milk | ~ 50 (??) |
| Almond milk (or oat milk, or other unsweetened nut milk) | 32 to 38 |
| Heme containing PX90 protein | 0.2 |
| Sugar | 9 |
| Vanilla Extract | 1 |
| Gelling agents (agar powder, cornstarch, and/or oleogel) | 2 to 10 |

Preparation is as Follows:
1. Preheat oven to 350° F. (175° C.)
2. For caramel: place 1 cup of sugar into a saucepan over medium-low heat, melt sugar until liquefied and light brown color. While hot, pour syrup into a round baking dish, make sure it is evenly spread over the whole dish.
3. Weight all ingredients
4. Mix all ingredients in a blender, until well blended.
5. Place the mixture into a round baking dish and cover with aluminum foil. Place the baking dish in a larger secondary container with water (water bath).
6. Place the dish in the secondary container in the oven for 60 min.

7. Refrigerate until cold
8. Once cold, carefully invert onto a serving plate.

Vegan Vanilla Cake

TABLE 6F

| Ingredients for cake | |
| --- | --- |
| | Quantity (% wt/wt) |
| Wheat flour | 25 to 35 |
| Sugar | 20 to 25 |
| Unsweetened nut milk or oat milk | 20 to 28 |
| Heme containing PX90 protein | 0.2 |
| Vegetable oil | 7 to 10 |
| Baking powder | 1 to 2 |
| Vanilla extract | 0.1 to 1.5 |
| Salt | 0 to 1.0 |
| Baking soda | 0 to 0.5 |
| Gelating protein in water or oleogel | 8 to 12 |

Preparation is as Follows:
1. Preheat the oven to 350° F. (175° C.).
2. Make the protein solution in water (concentration may range from 1.5-8%) depending in functionality
3. Mix wet ingredients (including the PX90 protein solution) and sugar in a stand mixer until sugar is well incorporated
4. In a separate bowl, weigh and mix the dry ingredients
5. Fold dry ingredients into the wet ingredients until well combined. Adjust the thickness by adding more flour
6. Place batter into a parchment lined pan.
7. Bake for 20-35 min at 350° F.
8. Let cool down at room temperature Creamy Mushroom Soup

TABLE 6G

| Ingredients for soup | |
| --- | --- |
| | Quantity (% wt/wt) |
| Mushrooms (sliced) | 35 |
| Vegetable broth | 26 |
| Heme containing PX90 protein | 0.2 |
| Coconut cream | 25 |
| Gelation casing protein in water solution/slurry (5 to 15% wt/wt) or oleogel | 9 |
| Coconut or avocado oil | 3 |
| onion powder | 1 |
| garlic powder | 1 |
| salt and pepper | |

Preparation is as Follows:
1. In a saucepan over medium-high heat, cook mushrooms in oil for about 5 to 7 min.
2, Add vegetable broth and seasonings, bring to a simmer.
3. On a separate cup, dissolve the gelation causing protein in water (5-5% wt/wt) depending on the desired thickness.
4. Stir in coconut cream and protein solution, and cook until the soup has thickened.
5. Season to Este with salt and pepper.

Frozen or Refrigerated Dough

A PX90 protein can be used to enhance the nutritional value of frozen and refrigerated doughs.

TABLE 6H

| Ingredients for frozen dough | |
| --- | --- |
| | Quantity (% wt/wt) |
| Water | 62.4 |
| Wheat flour | 28 to 33 |
| Heme containing PX90 protein | 0.2 |
| Yeast | 1.5 |
| Salt | 1.6 |
| Margarine (or other structured fat) | 1.5 |
| Gelation causing protein or oleogel | 1 to 5 |

Water should be adjusted based on the flour concentration and the PX90 protein. Preparation is as follows.

1. Mix ingredients, let rest for 10 minutes
2. Divide dough in 150 g each
3. Knead dough
4. Let proof at 28° C. and 85% until the dough volume increases.

Formulation and Regulatory Approval of PX90 Proteins as Food Ingredients

After a particular PX90 protein has been identified for further development as a food ingredient, the user will generally want to assure that all regulatory requirements are met before beginning manufacture, importation, or commercial distribution. For example, new food additives and products thereof for distribution in the U.S. are subject to premarket approval by the Food and Drug Administration (FDA). The new additives are "generally recognized as safe" (GRAS) if there is generally available and accepted scientific data, information, or methods indicating it is safe, optionally corroborated by unpublished scientific data. A notification sent to FDA's Office of Food Additive Safety for approval includes a succinct description of the substance (chemical, toxicological and microbiological characterization), the applicable conditions of use, and the basis for the GRAS determination. The FDA then evaluates whether the submitted notice provides a sufficient basis for a GRAS determination.

This disclosure describes and covers food products and supplements under development before approval, and food products and supplements that are formulated and approved by regulatory authorities for human consumption in a country or state where the food product is manufactured or sold. The formulation will include other ingredients that are all deemed manufactured and combined in a manner that is suitable for human consumption.

Pursuant to its obligations under the World Trade Organization (WTO), the FDA works with foreign governments and international standard-setting bodies to harmonize food safety laws, regulations and standards based on science. The FDA also establishes arrangements with regulatory partners to harmonize food safety standards and eliminate duplication or overlap in food safety controls. The FDA maintains two mechanisms in furtherance of these efforts: 1) Systems Recognition—whereby the FDA recognizes that a foreign food safety system achieves food safety outcomes comparable to those of the FDA; and 2) Equivalence—whereby the FDA recognizes that a foreign food safety system achieves the same level of public health protection as the U.S. despite having different food safety controls.

Equivalence is the process of determining whether a country's food safety controls achieve at least the same level of public health protection as measures required by U.S. law. This means that a foreign country is not required to develop and implement the same exact procedures and food safety controls that FDA requires, but rather the country must objectively demonstrate how its food safety controls meet at least the same level of public health protection achieved by U.S. measures.

Food regulatory and advisory agencies outside the U.S. include Health Canada and the Canadian Food Inspection Agency, the State Food and Drug Administration of China (SFDA), the Food Safety and Standards Authority of India, the Ministry of Food and Drug Safety (MFDS) in Korea, the European Food Safety Authority, the Federal Ministry of Food, Agriculture and Consumer Protection in Germany, the Food Standards Agency in the United Kingdom, and Food Standards and Safety in Australia.

Regulatory Approval of Pharmaceutical Products

A drug or pharmaceutical product is a composition that contains at least one active agent that requires regulatory approval and provides pharmacological activity or other direct effect in the diagnosis, cure, mitigation, treatment, or prevention of disease, or to affect the structure or any function of the body of man or animals. A nutraceutical product is any substance or ingredient that is promoted as providing a health benefits, but not regulated by the Food and Drug Administration in the U.S.

FDA approval of a drug requires that the drug's effects have been tested for safety and efficacy in clinical trials or their equivalent, and reviewed by the FDA's Center for Drug Evaluation and Research (CDER). The drug is determined to provide benefits that outweigh its known and potential risks for the intended population. The drug approval process takes place within a structured framework that includes:

1. Analysis of the target condition and available treatments-FDA reviewers analyze the condition or illness for which the drug is intended and evaluate the current treatment landscape, which provide the context for weighing the drug's risks and benefits. For example, a drug intended to treat patients with a life-threatening disease for which no other therapy exists may be considered to have benefits that outweigh the risks even if those risks would be considered unacceptable for a condition that is not life threatening.
2. Assessment of benefits and risks from clinical data-FDA reviewers evaluate clinical benefit and risk information submitted by the drug maker, taking into account any uncertainties that may result from imperfect or incomplete data. Generally, the agency expects that the drug maker will submit results from two well-designed clinical trials, to be sure that the findings from the first trial are not the result of chance or bias. In certain cases, especially if the disease is rare and multiple trials may not be feasible, convincing evidence from one clinical trial may be enough. Evidence that the drug will benefit the target population should outweigh any risks and uncertainties.
3. Strategies for managing risks—Risk management strategies include an FDA-approved drug label, which clearly describes the drug's benefits and risks, and how the risks can be detected and managed. In some circumstances, a drug maker may need to implement a Risk Management and Mitigation Strategy (REMS).

INCORPORATION BY REFERENCE

Each and every publication and patent documents cited in this disclosure are hereby incorporated herein by reference in their entireties for all purposes to the same extent as if each such publication or document was specifically and individually indicated to be incorporated herein by reference.

Interpretation and Implementation

Although the technology described above is illustrated in part by certain concepts, procedures, and information, the claimed invention is not limited thereby except with respect to the features that are explicitly referred to or otherwise required. Theories that are put forth in this disclosure with respect to the underlying mode of production, action, and assessment of various products and components are provided for the interest and possible edification of the reader, and are not intended to limit practice of the claimed invention.

While the PX90 proteins described in this disclosure were developed by the inventors and the owner of this technology as iron carrying flavorings and nutritional agents with superior properties, the PX90 proteins referred to in the claims that follow may be used in the manufacture of food or nutraceuticals for any reason, including but not limited to improving nutrition and/or flavor. Information about the physiological role of PX90 proteins in its natural context is historical, and does not limit the use of the PX90 protein, its homologs or any other product that falls within the definition of the PX90 protein as a food ingredient unless explicitly stated otherwise. The reader may use the technology put forth in this disclosure for any suitable purpose.

While the invention has been described with reference to the specific examples and illustrations, changes can be made and substituted to adapt to a particular context or intended use as a matter of routine development and optimization and within the purview of one of ordinary skill in the art, thereby achieving benefits of the invention without departing from the scope of what is claimed below and equivalents thereof.

SEQUENCE LISTING

```
Sequence total quantity: 41
SEQ ID NO: 1               moltype = AA   length = 227
FEATURE                    Location/Qualifiers
source                     1..227
                           mol_type = protein
                           organism = unidentified
SEQUENCE: 1
TKPGYINAAF RSSKNNEAYF FINDKYVLLD YAPGSSRDKV LYGPTPVRDG FKSLNQTIFG   60
SYGIDCSFDT ENNEAFIFYE NFCALIDYAP HSKKDKIILG PKKIADVFPF FEGTVFESGI  120
DAAYRSTRGK EVYLFKGDQY ARIDYGSNSM VNKEIKSISS GYPCFRNTIF ESGADAAFAS  180
HKTNEVYFFK DDHYARVKVT PGGKLAIMDG VREIVDYWPS LKDIVPL               227

SEQ ID NO: 2               moltype = AA   length = 225
FEATURE                    Location/Qualifiers
source                     1..225
                           mol_type = protein
                           organism = unidentified
SEQUENCE: 2
APYINAAFRS SSEYEVYFFA KNKYVRLHYT PGASSDTILT NLRLISSGFP SLAGTPFAEP   60
GIDCSFHTEA SEAYVFSGNH SAYIDYAPGT TNDKILVGPT TIAEMFPVLN NTVFEDSIDS  120
AFRSTKGKEV YLFKGNKYVR IAYDSKQLVG NIRNIGDGFP VLNGTEFESG IDACFASHKE  180
PEAYLFKGQN YVRIDFTPGG KADTLVGNIR PILDGWPVLK GIFPV                 225

SEQ ID NO: 3               moltype = AA   length = 231
FEATURE                    Location/Qualifiers
source                     1..231
                           mol_type = protein
                           organism = unidentified
SEQUENCE: 3
MTKTGYINAA FRSSQNNEAY LFINDKYVLL DYAPGTSNDK VLYGPTPVRD GFKSLNQTVF   60
GSYGVDCSFD TDNDEAFIFY EKFCALIDYA PHSNKDKIIL GPKKIADMFP FFEGTVFENG  120
IDAAYRSTRG KEVYLFKGDQ YARIDYETNS MVNKEIKSIR NGFPCFRNTI FESGTDAAFA  180
SHKTNEVYFF KGDYYARVTV TPGATDDQIM DGVRKTLDYW PSLRGIIPLE N          231

SEQ ID NO: 4               moltype = AA   length = 272
FEATURE                    Location/Qualifiers
source                     1..272
                           mol_type = protein
                           organism = unidentified
SEQUENCE: 4
MSNLPYINAA FRFSSRDYEV YFFAKNKYVR LQYTPGKTED KILTNLRLIS SGFPSLAGTP   60
FAEPGIDSAF HTEASEAYVF SANNRAYIDY APGTTNDKIL AGPTTIAEMF PVLRNTVFAD  120
SIDSAFRSTK GKEVYLFKGN KYVRIDYDSK QLVGSIRNIS DGFPVLNGTG FESGIDASFA  180
SHKEPEAYLF KGDKYVRIHF TPGKTDDTLV GDVRPILDGW PVLKAFCLCE LNKPSLSCIN  240
HLSLVTINKA FISNVCLFFF NVTLGLEACF LS                              272

SEQ ID NO: 5               moltype = AA   length = 463
FEATURE                    Location/Qualifiers
source                     1..463
                           mol_type = protein
                           organism = unidentified
SEQUENCE: 5
MYRWSRKPYQ EIFTNGFQAP DQGNADNNIY HDLDGFVHSV GVPVDPNRAV PRAFISTTIN   60
NAWRPNPSTD VLPIGSQIQL YRYEIFAPGG IWSAVTLKGR YQNPNLAEIT FVAGIAPQYI  120
CSVQMYTATR PRGDGFPTMT REIKLIMNSH FLPHMDLHFT IYTPLTYYKD DNGMRRELPK  180
```

```
ETYTPHESKV HKREVSSSQD NEEVGLHSYG AVEATPIYIN AAFRASANNE AYLFMNDECV  240
LINYGRGSTN DHIVNGPLYI YDGYPSLSRT PFGEHGIDCA FDTDKTQAYI FSANLCALID  300
YAPRTTDDKI VSGPMTITDM FPFFKDTVFE RGLDAAFRAH SSNEAYLFRG GHYALINYSS  360
KKLIHIETIR HGFHSLIGTV FENGVEAAFA SHATKEAYLF KGEYYANIYY APGTTDDYLI  420
GGRVKPILSN WPSLSSILPR DNGRLDLRSH KDHTDEDYGP VEL                    463

SEQ ID NO: 6           moltype = AA  length = 342
FEATURE                Location/Qualifiers
source                 1..342
                       mol_type = protein
                       organism = unidentified
SEQUENCE: 6
MARHAVAAVL LLVALSPIVH GEADQEAVPA YVEYSGGDAA GTPVAIVPPY LDGAAARDEP  60
AAAKSYLPAV AASPEGPVIP VYDDAADQHG FLRFPCRYRH HMRHGGFYRH RHGHEGFHGK  120
EEKQKLVFEM PVEPATRGEE RREEEEGVVL PVAEPVPDSR RQDAAVAAAE EEDEDEMARL  180
HHGRRSHHHH HRHHHHHHDE HEEDDHEQAD EASPAVERLI SFHHRRHHHH EEDNHEQREE  240
GAPMKRFRRQ HHHYEEESEM RTKRFHQHHH KDDDERELEE MARRWIRKAL MSSRMHHHRG  300
CRFHHHHHHL SFRHRAEDAA AAGEEEEKGG VMSWLKDFVN RF                     342

SEQ ID NO: 7           moltype = AA  length = 227
FEATURE                Location/Qualifiers
source                 1..227
                       mol_type = protein
                       organism = unidentified
SEQUENCE: 7
TKTGYINAAF RSSRNNEAYL FINDKYVLLD YAPGTSNDKV LYGPSFVRDG YKSLAKTIFG  60
TYGIDCSFDT EYNEAFIFYE NFCARIDYAP HSDKDKIISG PKKIADMFPF FKGTVFENGI  120
DAAFRSTKGK EVYLFKGDKY ARIDYLTNRL VQNIKSISDG FPCLRGTIFE AGMDSAFASH  180
KTNEAYLFKG EYYARINFTP GSTNDIMGGV KKTLDYWPSL RGIIPLE               227

SEQ ID NO: 8           moltype = AA  length = 37
FEATURE                Location/Qualifiers
source                 1..37
                       mol_type = protein
                       organism = unidentified
SEQUENCE: 8
TLTGYIANFS VLNXEAYLFI NDKYVLLDYA PGTXNDK                          37

SEQ ID NO: 9           moltype = AA  length = 231
FEATURE                Location/Qualifiers
source                 1..231
                       mol_type = protein
                       organism = unidentified
SEQUENCE: 9
MSTPARAAFL RPGKPEECYF FQGDQYIRML ITPGATNDKL LYGPAKIMDE WPSLKQAGFN  60
SIDACLPSPK DDSEVYFFSG DQYCLIKVVP ESSNDKIITG PKSIADYWPS LKKAGFTTLE  120
EVFPSPRGDG ETYCFKDSNY CRIKFVPGTL DESLMNGPTD IQAGWPSLKQ VGFSSIDVAV  180
VNYKDPSQVY CFNGNQYARI HVVPGTSDDT VIDGPHDVAS RWPALKQAGF Y           231

SEQ ID NO: 10          moltype = AA  length = 225
FEATURE                Location/Qualifiers
source                 1..225
                       mol_type = protein
                       organism = unidentified
SEQUENCE: 10
ASYINAAFRS SRAYEVYFFE CNKYVRVYYT PGKTDDKILT NLRLISSGFP SLAGTAFAEP  60
GIDCSFDTEA SEAYVFSGSQ CAYIDYAPGT TNDKILSGPT TIAEMFPVLK NTVFEDGIDS  120
AFRSTKGKEV YLFKGNKYGR IAYDSKQLVG TIRNITDGFP VLKGTIFESG IDASFASHKE  180
PEAYLFKGAQ YVRIKFTPGA TNNTLTGKVR PILDGWPCLR DILPT                 225

SEQ ID NO: 11          moltype = AA  length = 166
FEATURE                Location/Qualifiers
source                 1..166
                       mol_type = protein
                       organism = unidentified
SEQUENCE: 11
MNQLQQLQNP GESPPVHPFV APLSYLLGTW RGQGEGEYPT IPSFRYGEEI RFSHSGKPVI  60
AYTQKTWKLE SGAPMHAESG YFRPRPDGSI EVVIAQSTGL VEVQKGTYNV DEQSIKLKSD  120
LVGNASKVKE ISREFELVDG KLSYVVRMST TTNPLQPHLK AILDKL                166

SEQ ID NO: 12          moltype = AA  length = 223
FEATURE                Location/Qualifiers
source                 1..223
                       mol_type = protein
                       organism = unidentified
SEQUENCE: 12
MKNNKPSISF SFISLFLLVS AVAVSAINDE EPVKDTNGNP LKIETRYFIQ PASDNNGGGL  60
VPANVDLSHL CPLGIVRTSL PYQPGLPVTI STPSSSEGND VLTNTNIAIT FDAPIWLCPS  120
SKTWTVDSSS EEKYIITGGD PKSGESFFRI EKYGNGKNTY KLVRYDNGEG KSVGSTKSLW  180
```

-continued

```
GPALVLNDDD DSDENAFPIK FREVDTSKGS VFKKSSLRMF PFV                        223

SEQ ID NO: 13              moltype = AA   length = 726
FEATURE                    Location/Qualifiers
source                     1..726
                           mol_type = protein
                           organism = unidentified
SEQUENCE: 13
MRSSSLAWAL GLVALANAQG SPTQWYDSIT GVTFSRFYQQ DTDASWGYIF PSASGGQAPD      60
EFIGLFQGPA SAGWIGNSLG GSMRNNPLLV GWVDGSTPRI SARWATDYAP PSIYSGPRLT      120
ILGSSGTNGN IQRIVYRCQN CTRWTGGAGG IPTTGSAVFG WAFHSTTKPL TPSDPSSGLY      180
RHSHAAQYGF DIGNARTTLY DYYLQQLTNA PPLSGGAPTQ PPTQQPPTTT APPPPPPSST      240
FVSCPGAPQP RYQMNVANGF RVAPVLGGLT MPRGITLDTR GNLLVVERGR GLTGHTLDAN      300
GCVTSSKVVI QDTQINHGID VHPSGRRIIA SSGDIAWSWD YDPATMTATN RRTLVTGMNN      360
FYHFTRTVHI SRKYPNLFAL NVGSDGNIDV PTRQQNSGRA QIRVFDYDQL PQNGVPFVSQ      420
YGRVLGYGLR NDVGITEDRA GNIHSIENSL DNAYRMVNGQ RRDIHTNNPA EKVYNLGDPS      480
NPRAIFGGYP DCYTVWEPSD FTDSPKQPGD WFTQDNSGQY TDAWCNANAV KPTLLLPPHT      540
APLDMKFGLG NDTNLYVALH GSWNRQPPQG YKVVVVPGQY SASGEWSPTA PLAQSRTAWS      600
DLLTNRNENQ CSGFGNANCF RPVGLVWSAD GQNLYVSSDT SGEVFIIKRM SGPIVQPPIT      660
QPPITTSPPT PTTPPVVQPP TTVAPPQASQ TLWGQCGGQG WTGPTLCPAN SVCRESNQWY      720
SQCVPA                                                                726

SEQ ID NO: 14              moltype = AA   length = 261
FEATURE                    Location/Qualifiers
source                     1..261
                           mol_type = protein
                           organism = unidentified
SEQUENCE: 14
MKSLSFSLAL GFGSTLVYSA PSPSSGWQAP GPNDVRAPCP MLNTLANHGF LPHDGKGITV      60
NKTIDALGSA LNIDANLSTL LFGFAATTNP QPNATFFDLD HLSRHNILEH DASLSRQDSY      120
FGPADVFNEA VFNQTKSFWT GDIIDVQMAA NARIVRLLTS NLTNPEYSLS DLGSAFSIGE      180
SAAYIGILGD KKSATVPKSW VEYLFENERL PYELGFKRPN DPFTTDDLGD LSTQIINAQH      240
FPQSPGKVEK RGDTRCPYGY H                                                261

SEQ ID NO: 15              moltype = AA   length = 371
FEATURE                    Location/Qualifiers
source                     1..371
                           mol_type = protein
                           organism = unidentified
SEQUENCE: 15
MKYFPLFPTL VFAARVVAFP AYASLAGLSQ QELDAIIPTL EAREPGLPPG PLENSSAKLV      60
NDEAHPWKPL RPGDIRGPCP GLNTLASHGY LPRNGVATPV QIINAVQEGL NFDNQAAVFA      120
TYAAHLVDGN LITDLLSIGR KTRLTGPDPP PPASVGGLNE HGTFEGDASM TRGDAFFGNN      180
HDFNETLFEQ LVDYSNRFGG GKYNLTVAGE LRFKRIQDSI ATNPNFSFVD FRFFTAYGET      240
TFPANLFVDG RRDDGQLDMD AARSFFQFSR MPDDFFRAPS PRSGTGVEVV IQAHPMQPGR      300
NVGKINSYTV DPTSSDFSTP CLMYEKFVNI TVKSLYPNPT VQLRKALNTN LDFFFQGVAA      360
GCTQVFPYGR D                                                          371

SEQ ID NO: 16              moltype = AA   length = 492
FEATURE                    Location/Qualifiers
source                     1..492
                           mol_type = protein
                           organism = unidentified
SEQUENCE: 16
MDPYKYRPSS SFNAPMWSTN SGAPVWNNDN SLTVGSRGPI LLEDYHLVEK IADFDRERIP      60
ERVVHARGAT AKGFFEVTHD VSHLTCADFL RAPGVQTPVI VRFSTVIHER GSPETLRDPR      120
GFAIKFYTRE GNWDLVGNNF PVFFIRDGMK FPDMVHALKP NPKTHIQENW RILDFFSHHP      180
ESLHMFTFLF DDIGVPADYR HMDGSGVNTY TLVNRAGKAH YVKFHWKPTC GVKSLLEEEA      240
VTVGGTNHSH ATKDLTDSIA AGNYPEWTFY IQTIDPDYEE RFDFDPLDVT KTWPEDVVPL      300
QPVGRLVLNR NIDNFFSENE QLAFCPGIIV PGVYYSDDKL LQTRIFSYSD TQRHRLGPNY      360
LLLPANAPKC SHHNNHYDGL MNFMHRDEEV DYFPSRFDPA KHAPRYPIPS RTLNGRREKM      420
VIEKENNFKQ PGERYRSMDP ARQERFINRW IDALSDPRLT HEIKAIWLSY WSQADKSLGQ      480
KLASRLSSKP SM                                                         492

SEQ ID NO: 17              moltype = AA   length = 344
FEATURE                    Location/Qualifiers
source                     1..344
                           mol_type = protein
                           organism = unidentified
SEQUENCE: 17
MSRPVKLFFL AFLALLAAVH GDLQIGFYNQ SCPSAESLVQ QAVAAAFANN SGIAPGLIRM      60
HFHDCFVRGC DASVLLDSTA NNTAEKDAAP NNPSLRGFEV IAAAKSAVEA ACPKTVSCAD      120
ILAFAARDSA ALAGNITYQV PSGRRDGNVS LASEALTNIP APTFNATQLI NSFAGKNLTA      180
DEMVTLSGAH SIGVSHCFSF LNRIYNFSNT SQVDPTLSSS YADLLRTKCP SNSTRFTPIT      240
VSLDIITPTV LDNRYYTGVQ LTLGLLTSDQ ALVTEANLSA AVKNNADNLT AWVAKFAQAI      300
VKMGQIQVLT GTQGEIRTNC SVVNSASLGD IVMASGHLTE VATS                      344

SEQ ID NO: 18              moltype = AA   length = 253
FEATURE                    Location/Qualifiers
```

```
source                 1..253
                       mol_type = protein
                       organism = unidentified
SEQUENCE: 18
MALSSSKFSS FSGFSLSPVS GNGVQKPCFC DLRVGEKWGS RKFRVSATTA PLTGVIFEPF    60
EEVKKDYLAV PSVPLVSLAR QNFADECESV INEQINVEYN ASYVYHSLFA YFDRDNVALK    120
GFAKFFKESS EEHREHAEKL MKYQNTRGGR VVLHPIKDVP SEFEHVEKGD ALYAMELALS    180
LEKLTNEKLL NVHSVAERNN DLEMTHFIEG EYLAEQVEAI KKISEYVAQL RRVGKGHGVW    240
HFDQRLLHGV HGA                                                       253

SEQ ID NO: 19          moltype = AA  length = 156
FEATURE                Location/Qualifiers
source                 1..156
                       mol_type = protein
                       organism = unidentified
SEQUENCE: 19
MKGKPAVLAQ LHKLLRGELA ARDQYFIHSR MYQDWGLEKL YSRIDHEMQD ETAHASLLIE    60
RILFLEETPD LSQQDPIRVG KTVPEMLQYD LDYEYEVIAN LKEAMAVCEQ EQDYQSRDLL    120
LKILADTEED HAYWLEKQLG LIEKIGLQNY LQSQMS                              156

SEQ ID NO: 20          moltype = AA  length = 237
FEATURE                Location/Qualifiers
source                 1..237
                       mol_type = protein
                       organism = unidentified
SEQUENCE: 20
MDSGEIRATP ARAAFLRPGK PEECYFFQGD QYIRMLITPG ATNDKLLYGP AKIMDEWPSL    60
KQAGFNSIDA CLPSPKDDSE VYFFSGDQYC LIKVVPESSN DKIITGPKSI ADYWPSLKKA    120
GFTTLEEVFP SPRGDGETYC FKDSNYCRIK FVPGTLDESL MNGPTDIQAG WPSLKQVGFS    180
SIDVAVVNYK DPSQVYCFNG NQYARIHVVP GTSDDTVIDG PHDVASRWPA LKQAGFY      237

SEQ ID NO: 21          moltype = AA  length = 227
FEATURE                Location/Qualifiers
source                 1..227
                       mol_type = protein
                       organism = unidentified
SEQUENCE: 21
TKPGYINAAF RSSKNNEAYF FINDKYVLLD YAPGSSRDKV LYGPTPVRDG FKSLNQTIFG    60
SYGIDCSFDT ENNEAFIFYE NFCALIDYAP HSKKDKIILG PKKIADVFPF FEGTVFESGI    120
DAAYRSTRGK EVYLFKGDQY ARIDYGSNSM VNKEIKSISS GYPCFRNTIF ESGADAAFAS    180
HKTNEVYFFK DDHYARVKVT PGGKLAIMDG VREIVDYWPS LKDIVPL                227

SEQ ID NO: 22          moltype = AA  length = 459
FEATURE                Location/Qualifiers
source                 1..459
                       mol_type = protein
                       organism = unidentified
SEQUENCE: 22
MARALRVPVA LWLLGLCWSL AKAHPLARAP ELGHGVEGGN VAKPDPEVTE RCSDGWGFDA    60
TTLDEHGNML FLKGEFVWKG HAWARQLISE RWKDAPSPVD AAFRYDRNSV LLIKGDKFWV    120
YPPEKGEEYP KLLQEKFPGI PFPLDAAVEC HRGECSHEGV FFFQGNHTWF WDFSTKTIKK    180
RSWPAVGNCS SAIRWLNRYY CFRGNKFLRF DPVTGEVNST YPRDVRDYFM SCPNRGHAHR    240
NATQHMDKRC SPHLVLSALL SDNHSATYAF SENHYWRLDS SRDGWHSWRI EHLWPQGPST    300
VDAAFLWDKK LYLIQGTQVY IFLTRAGYTL VKDYPKQLEK EFGSPDGVCL HSVDAAFTCP    360
GSSQLYIMAG QKLWRLDLNL GAQATWTELP WLHTKVDGAL CTEKSLGPHS CSANGLGLYL    420
VQGPNLYCYK DVEELSKTKD LPQAQRMNSL LGCAPHQHS                          459

SEQ ID NO: 23          moltype = AA  length = 151
FEATURE                Location/Qualifiers
source                 1..151
                       mol_type = protein
                       organism = unidentified
SEQUENCE: 23
MTVYTNTSLK AELNERGWRL TPQRETILHI FQELPQGEHL SAEDLYHRLE ADGEGISLST    60
IYRTLKLMAR MGILRELELG EGHKHYEINQ PYPHHHHHLI CVKCNSTIEF KNDSILKIGA    120
KTAQKEGFHL LDCQMTIHAV CPKCQRALMP L                                  151

SEQ ID NO: 24          moltype = AA  length = 311
FEATURE                Location/Qualifiers
source                 1..311
                       mol_type = protein
                       organism = unidentified
SEQUENCE: 24
MDIQNMPREQ LGVCAEGNLH SVYLMFNAND NVESQLRPCI ANVAQYIYEL TDQYSDSAFN    60
GFVAIGANYW DSLYPESRPE MLKPFPAMQE GNREAPAIEY DLFVHLRCDR YDILHLVANE    120
ISQMFEDLVE LVEEERGFRF MDSRDLTGFV DGTENPKGRH RQEVALVGSE DPEFKGGSYI    180
HVQKYAHNLS KWHRLPLKKQ EDIIGRTKQD NIEYESEDKP LTSHIKRVNL KDENGKSIEI    240
LRQSMPYGSL KEQGLMFIST CRTPDHFEKM LHSMVFGDGA GNHDHLMHFT SALTGSSFFA    300
PSLDFLMQFD N                                                        311
```

-continued

```
SEQ ID NO: 25              moltype = AA   length = 571
FEATURE                    Location/Qualifiers
source                     1..571
                           mol_type = protein
                           organism = unidentified
SEQUENCE: 25
MPFETSPADT LCRSAGCPHL SGAHLGRGSL EKEPPEDKEA KELLWIRPDA PSRCSWQLGR     60
PVADSPHCHA ALVKSPKILP DILKKIGDTP MVRINKIGRN FGLKCELLAK CEFFNAGGSV    120
KDRISLRMIE DAEREGTIKP GDTIIEPTSG NTGIGLALAA AVKGYRCIIV MPEKMSTEKV    180
DVLRALGAEI VRTPTNARFD SPESHVGVAW RLRNEIPNSH ILDQYRNASN PLAHYDITAE    240
EILQQCDGRL DMLVASAGTG GTITGVARKL KEKCPGCKIV GVDPEGSILA EPEELNQTEQ    300
TAYEVEGIGY DFIPTVLDRT VVDKWFKSND EEAFAFARML IAQEGLLCGG SSGSAMSVAV    360
KAAQELQEGQ RCVVILPDSV RNYMSKFLSD KWMLQKGFMK EEEISVKRPW WWHLQVQELS    420
LSAPLTVLPT VTCEHTIEIL REKGFDQAPV VDESGVILGM VTLGNMLSSL LAGKVQPSDQ    480
VCKVIYKQFK QIYLTDPLGK LSHILEMDHF ALVVHEQIQY RCHGESSKRQ MVFGVVTAID    540
LLNFVATRER NQRTKPESAL KLGGVGAEAQ L                                  571

SEQ ID NO: 26              moltype = AA   length = 289
FEATURE                    Location/Qualifiers
source                     1..289
                           mol_type = protein
                           organism = unidentified
SEQUENCE: 26
MERPQPDSSM PQDLSEALKE ATKEVHTQAE NAEFMKNFQK GELTQEGFKL VMASLYHIYV     60
ALEEEIERNK ENPVYTPLYF PEELHRRASL EQDMAFWYGP RWQEAIPYTQ ATKRYVQRLQ    120
EVGRTEPELL VAHAYTRYLG DLSGGQVLKK IAQKALNLPS SGEGLAFFTF PNIASATKFK    180
QLYRSRMNTL EMTPEVRQRV LDEAKTAFLL NIQLFEELQG LLTQKAKDHD PLQAPELHRR    240
AGSKVQDLAP TKASRGKPQP SVLSQAPLLR WVLTLSFLVA TVAVGLYAM                289

SEQ ID NO: 27              moltype = AA   length = 227
FEATURE                    Location/Qualifiers
source                     1..227
                           mol_type = protein
                           organism = unidentified
SEQUENCE: 27
MKNILKVFNT TILALIIIIA TFSNSANAAD SGTLNYEVYK YNTNDTSIAN DYFNKPAKYI     60
KKNGKLYVQI TVNHSHWITG MSIEGHKENI ISKNTAKDER TSEFEVSKLN GKIDGKIDVY    120
IDEKVNGKPF KYDHHYNITY KFNGPTDVAG ANAPGKDDKN SASGSDKGSD GTTTGQSESN    180
SSNKDKVENP QTNAGTPAYI YAIPVASLAL LIAITLFVRK KSKGNVE                  227

SEQ ID NO: 28              moltype = AA   length = 188
FEATURE                    Location/Qualifiers
source                     1..188
                           mol_type = protein
                           organism = unidentified
SEQUENCE: 28
MAFSVNYDSS FGGYSIHDYL GQWASTFGDV NHTNGNVTDA NSGGFYGGSL SGSQYAISST     60
ANQVTAFVAG GNLTYTLFNE PAHTLYGQLD SLSFGDGLSG GDTSPYSIQV PDVSFGGLNL    120
SSLQAQGHDG VVHQVVYGLM SGDTGALETA LNGILDDYGL SVNSTFDQVA AATAVGVQHA    180
DSPELLAA                                                            188

SEQ ID NO: 29              moltype = AA   length = 345
FEATURE                    Location/Qualifiers
source                     1..345
                           mol_type = protein
                           organism = unidentified
SEQUENCE: 29
MSKSIYEQYL QAKADNPGKY ARDLATLMGI SEAELTHSRV SHDAKRLKGD ARALLAALEA     60
VGEVKAITRN TYAVHEQMGR YENQHLNGHA GLILNPRNLD LRLFLNQWAS AFTLTEETRH    120
GVRHSIQFFD HQGDALHKVY VTEQTDMPAW EALLAQFITT EIPELQLEPL SAPEVTEPTA    180
TDEAVDAEWR AMTDVHQFFQ LLKRNNLTRQ QAFRAVGNDL AYQVDNSSLT QLLNIAQQEQ    240
NEIMIFVGNR GCVQIFTGMI EKVTPHQDWI NVFNQRFTLH LIETTIAESW ITRKPTKDGF    300
VTSLELFAAD GTQIAQLYGQ RTEGQPEQTQ WRDEIARLNN KDIAA                    345

SEQ ID NO: 30              moltype = AA   length = 178
FEATURE                    Location/Qualifiers
source                     1..178
                           mol_type = protein
                           organism = unidentified
SEQUENCE: 30
MGSSHHHHHH SSGEAAGAGT PTQPPAPHPA VAPLAFLLGK WRGEGEGSFP TISSFRYGEE     60
LLFSHHPSKP VISYAQKTWK AASGEPMHAE SGYWRPRPDG TVEVVIAQST GLAEIQKGSY    120
DAEKKMVTLQ SELVGNASKV KQITRAFQVA DGELSYIVQM ATITTSLQPH LKALLKKI     178

SEQ ID NO: 31              moltype = AA   length = 477
FEATURE                    Location/Qualifiers
source                     1..477
                           mol_type = protein
```

```
                          organism = unidentified
SEQUENCE: 31
MGSSHHHHHH SSGPALIETC VPATSTQETI SRKYDVTQNG FLPSSAPLRR LTDPYYALWE   60
LLAEKLPELL ERKLLRYIVD SSQVLSTDRL QSEEEWRRAY VVLVFLAHGY IWGGDRPSEV  120
LPPQITVPLL KLAEHFDLPP CATYAGLVLW NFETLNNDSD FSDPDNLRAI NTFTGTESES  180
WFYMISVALE AQSAWVMPLM VDAIEATHSR DYAKMKKGLE QIIIAIKKMD ELLKRMYEKC  240
DPALFYDKIR PFLAGSANME AAGLPNGVFY DEGDGKGSWR KLMGGSNGQS SLIQFFDVVL  300
GVEHTGGADK ASVPKVCPVS GMATEESTSG CPVSAGKEKN MGYHEKVRAY MPEPHRRFLR  360
SLARMGSLQA FASTPQPDAE FEQVKELYQL ACKTMGDFRC THIQVVTKYI IIQARKQPVG  420
ETLNLAKASS ASDGSDLKGT GGTSLAAFLK QSRDESYEAG RVPDQPAPGV SSEYAVM     477

SEQ ID NO: 32          moltype = AA  length = 655
FEATURE                Location/Qualifiers
source                 1..655
                       mol_type = protein
                       organism = unidentified
SEQUENCE: 32
MGSSHHHHHH SSGLQGRIAA VDQRTSVRRS GMHVRRDARA GSVRSAAAVL WARPDAQGFL   60
PAIEPQVRIQ LDDPAVQEWE QALHELPGAF GAGSGTQLRE RLRRLPPFPT DRLLPPWTSP  120
GRIPSLQPPL ACIGGGGTGG SRSGGGGSG GGGMTGDVED RLLLPAQDAA DHPPAGAVEP   180
EAPTSGGFLD DGNAWRAYLV LSFLAHAYVW CEPGPPPAVL PAVLAVPWAR VAAAVGMPPI  240
LTYATYNLYN WRRLNPELPP VLQNLSSINN FLGGPDEEWF RLVHVDIETR AGPAVAGLAR  300
LQQAAAQDDA GAVLMGLSAI SESLRAMQTT LARIGECCDP DQYYSRVRPP IAGWRNNPLL  360
PYGLVYEGVY GGAPVQLYGA TGAQSSVVPA FDRVLDIRHE QGRLRDYLGT MVAHMPPPHR  420
AFLAALAAAN NNTGTGTGNR TNSGASTNSS GGAGRGQDGG AGQPVAAANV RAYVLAAAAT  480
GSGHPRGGEL RDAYDCTVGE LDRFRSLHRS VAQRYIVQPA TATTTAPAST ATATTTAPAS  540
ASASASTAAS TSTSAHLHTH ATSITAVGST AAGAASPSAP PPPPPAPLPT RGGVGQPDGL  600
LASGTLASGV AAAVGTAVET AVALAGVTGT GGSDVIPALT AFRDATRRHK IARSD       655

SEQ ID NO: 33          moltype = AA  length = 318
FEATURE                Location/Qualifiers
source                 1..318
                       mol_type = protein
                       organism = unidentified
SEQUENCE: 33
TTMTGQISAE AQRVDAPLTQ SATFLVLSLL DRPDTVHTVR STLANLESLS KNVSIRDPSA   60
SFTCTTGIGS DAWDRLTGHP RPAELHPFPE VKGARHTAVS TPGDLLFHIR SERRDLCFEF  120
ERQLLDCLGD TIVVVDETVG FRYFDLRDLL GFVDGTANPV GAAVPSSTLV AEEDVAACGG  180
SYIVVQKYVH DIKTWRALSV EQQEAIIGRT KVENVELDDA PADHQQAHKS LSTITDENGV  240
EHSILRDNMP FGSPGSGEFG TYFIGYSRRL WVIEQMLQRM FVGSPPGSHD RLLDFSTPLT  300
GTTFFAPSLD FLRNLSPE                                               318

SEQ ID NO: 34          moltype = AA  length = 325
FEATURE                Location/Qualifiers
source                 1..325
                       mol_type = protein
                       organism = unidentified
SEQUENCE: 34
MGSSHHHHHH SSGKASSRAQ AVDGPLTQSA SFVVLTVADG AEAIKTVRSV LSGLSGVAKS   60
VGMRDSTGSL ACTVGIGSRV WDKLMGMPRP AELRAFKEIK GKRHTAVSTP GDLLLHIRSD  120
RRDICFEFER QVMKQLGSAV QVQDATVGFR YFDLRDLLGF VDGTANPVGP AVPDAVLVAE  180
EDDERSAGGS YIVVQKYHHN LEAWEKLSTE KQEAVIGRTK LDNMELDDAP AAAQKSHKTL  240
ATIEDEEGNE HDILRDNMPF GSPGTQEFGT YFIGYSRRLW VVERMLERMF IGDPPGLHDG  300
ILDFSEAKTG SVFFAPSADV LAGLD                                       325

SEQ ID NO: 35          moltype = AA  length = 383
FEATURE                Location/Qualifiers
source                 1..383
                       mol_type = protein
                       organism = unidentified
SEQUENCE: 35
MGSSHHHHHH SSGERLSIVP IIARSGHTTE PIPLSKIGHR TPILSPFIHD HHHRPLHTAP   60
TPSHPPTMSR TSLRPQRVDA PLTQFATFLV LTLDPSPPSL STVRTTLASL SDLTKNITIR  120
DPSAHFTCTV GIGSTIWDDL TRLPRPSELR PFPEIPGPKH TAISTPGDLL FHIRSERRDL  180
CFEFERQLLD RLGHTVTVVD ETEGFRYFDM RDLLGFVDGT ANPVGPAVPD AVLITKNTDP  240
AAAGGSYIVI QKYLHDLSAW KSLPIEHQER IIGRTKLENI ELADAEDGAQ QSHKSLATIE  300
DENGEEYAIV RDNMPFGAPG KGEFGTYFIG YTARLWVIEK MLERMFVGEP RGKYDRILDF  360
SVPKTGGTFF APGGGVLDSL DDH                                         383

SEQ ID NO: 36          moltype = AA  length = 516
FEATURE                Location/Qualifiers
source                 1..516
                       mol_type = protein
                       organism = unidentified
SEQUENCE: 36
MGSSHHHHHH SSGTTPAPPL DLNNIQGDIL GGLPKKTETY FFFDVTNVDR FKANMTQFIP   60
HVKTSAGIVK DREAIKEHKR QKRPGLVPMA AVNVSFSHLG LQKLGITDDL SDSSFTTGQR  120
KDAEVLGDPG TKNGDTFTPA WEAPFLKDIH GVIFVAGDCH ASVHKKLDEI KHIFGVGTSH  180
ASISEVTHVR GDVRPGQVSA HEHFGFLDGI SNPAVDQFDQ NPFPGQDSIR PGFILAKENG  240
```

-continued

```
DSRAAARPDW AKDGSFLTFR YLFQMVPEFD DFLESNPIVL PGLSRKEGSE LLGARIVGRW   300
KSGAPIEITP LKDDPKLGAD AQRNNNFDFG DSLVRGDQTK CPFAAHIRKT YPRNDLEGPP   360
LNADIDNRRI IRRGIQFGPE VTSQEHHDKK THHGRGLLFV CYSSSIDDGF HFIQQSWANA   420
PNFPVNAVTS AGPIPPLDGV IPGFDAIIGQ KVGGGIRQIS GTNPNDPTTN ITLPDQDFVI   480
PRGGEYFFSP SISALKTKFA AGVASSAPQA QAPIST                            516

SEQ ID NO: 37              moltype = AA   length = 204
FEATURE                    Location/Qualifiers
source                     1..204
                           mol_type = protein
                           organism = unidentified
SEQUENCE: 37
MGSSHHHHHH SSGRKESNRR SDQQKKSPGI ETETPKKMEG GGAPAPAAPP PAPHPAVAPL   60
AFLLGKWRGE GEGSFPTISP FRYGEELVFS HHPSKPVISY TQRTWKPASG EPMHAESGYW   120
RPRPDGSVEV VISQSTGLAE VQKGSFDAEK KTLTLQSELV GNASKVKQIT RAFQLVDGEL   180
SYVVQMATIT TSLQPHLKAL LKKI                                         204

SEQ ID NO: 38              moltype = AA   length = 178
FEATURE                    Location/Qualifiers
source                     1..178
                           mol_type = protein
                           organism = unidentified
SEQUENCE: 38
MGSSHHHHHH SSGNQLQQLQ NPGESPPVHP FVAPLSYLLG TWRGQGEGEY PTIPSFRYGE   60
EIRFSHSGKP VIAYTQKTWK LESGAPMHAE SGYFRPRPDG SIEVVIAQST GLVEVQKGTY   120
NVDEQSIKLK SDLVGNASKV KEISREFELV DGKLSYVVRM STTTNPLQPH LKAILDKL    178

SEQ ID NO: 39              moltype = AA   length = 516
FEATURE                    Location/Qualifiers
source                     1..516
                           mol_type = protein
                           organism = unidentified
SEQUENCE: 39
MGSSHHHHHH SSGTARSQAT NTQKRPKVQC SATTKQLLFN QVTPDRAFLP AQDPLLRLPP   60
GLQAYEDALQ ELPKLTLGSP GFLRQTLQDL PCFDLQQLPA LASCDTAQLL QQLPPACQCY   120
TAAAGTSSSS SSSPQQSTAD VLRSFPSCDA QLWRAYMVLA FLTHGFLWCD GPGVPSVLPH   180
LLAGFLWCDG PGVPSVLTQL LAQPFAAVSA AIGMPPVLTY ATYNLMNWRR LDPAAPLELG   240
NICCQHNFFG GMDEEWFRLI HVAIEAAAAP AIAALQPLQQ AALQHDAAAM ELHFAAITSA   300
LQAMQELLAR MGERCDPYVY YKRVRVPMSG WRNNEALPQG LVYEGLWGNQ PQQLYGETGA   360
QSTVVHALDA ALGIQHTKGW MQAYLTDMRA HMPPSHRAFL HQLEQEPSVR DAVQALAQTT   420
TSSSSSNNNS SGSNKSSSSS SLVEAYDAAI AELERFRSQH RAFAIAYIAQ WSKKEAKEVG   480
TGGSDFVPAL SAYKDATAAH KLAGSSSSSR GCPLHS                            516

SEQ ID NO: 40              moltype = AA   length = 500
FEATURE                    Location/Qualifiers
source                     1..500
                           mol_type = protein
                           organism = unidentified
SEQUENCE: 40
MGSSHHHHHH SSGLPPIPAL ADYGISADHG FLPPEPPLEI LPDPYYAKWE WVVSNLQALL   60
TSRRIREVVD HMSTLSTSYL QTENEWRRAY VVLVFMLHGY VWGGSKPAEK IPPQLTVPLF   120
DVCEHLGLPP VATYAGVCLW NYKPIFPEEP IDDLRNLDTV NTFTGSLDEK WFYLVSVAIE   180
ARGAPSIPLV LQAIAAARAG NSLVVTECLQ RLAEVLDEVG SLLERMYEHC DPYVFYHRIR   240
PYLAGSKNMA DAGLPHGLLY DNGSGQPEYR QYGGGSNAQS SLIQFFDIAL GIEHRPTGET   300
RPSSSPVKDE KEGVAGAPRH GFIQEMRTYM PAAHRRFLEH INAVANIRQY VEARRSDKAL   360
CIAYDACLSM LRAMRDKHIQ IVSRYIIIQS RDARPSRPAR ATSPKRAINL ATARHGEKPD   420
SKKLRGTGGT ALIPFLKQAR DETGEPAIDA WARRLLSTGP SESSFAALSK VDEDHDGHLQ   480
VVGLSGTWAA DDSEGGICHW                                              500

SEQ ID NO: 41              moltype = AA   length = 482
FEATURE                    Location/Qualifiers
source                     1..482
                           mol_type = protein
                           organism = unidentified
SEQUENCE: 41
MGSSHHHHHH SSGRSMQPLI LFVLGSLAII VFWKSIVQPF IQSWLQTLPK SDIRKEKSDA   60
IKDLAEHHEV AEILSELIQK DGAGSWPPNA NHAHTEWPLC IQPYREIYLE MAPLLPQPEP   120
SLDDEVNASR ISEFRQRYRD LLSERVDLVE VKKLMDMAEA DRWVEFPRDV YNAFYCCIAS   180
TRHAYRWATI PVVKVAQLEK VVELPVELTM PWESMQRHFG CPSDGGNVTC NLLLNFDKTG   240
SYIYKINTGM APRILAAEEA FSRIFYDLES LSLPVYHDMA QAIIALDRGD TAACARHVAS   300
ITAQMQGVIA TYTTKLHDKF IAHSIWLSRI QGFFGWGAGH YNTETNEWEK YDGLSGNQLL   360
LFPAMDAFLG IEQYLSQRDQ EMSVPRRQRE LCHALRKHSF RARLAKMDGD IHVAEILHNF   420
DMILKQLRLF RAAHRTRAKT YLSQPAPERL PMTAGKSLLK PSIEDSFEFL DKFMVRRLGQ   480
TV                                                                482
```

The invention claimed is:

1. A food product or flavor additive comprising:

0.2% to 5% by weight of a heme-containing or porphyrin binding PX90 protein containing iron;

a protein content of at least 10% by weight, wherein at least 75% of the protein content is a mixture of plant proteins; and a fat content of at least 5% by weight, wherein at least 75% of the fat content is an oleogel or one or more plant derived oils; and wherein after cooking, the food product or a product made from the flavor additive has a meat-associated aroma and/or taste;

wherein the PX90 protein comprises a THAP4-like heme-binding beta-barrel domain or a heme binding portion thereof.

2. The food product or flavor additive of claim 1, wherein the PX90 protein is a full-length or splice variant of a naturally occurring heme-containing or porphyrin binding protein that has been recombinantly expressed in a plant, yeast, or other microbe.

3. A method of improving nutritional value of a nutritional supplement or food product, comprising compounding the nutritional supplement or food product so that it contains 0.10% to 10% by weight of a PX90 protein bound to a porphyrin ring or heme that contains an iron atom.

4. A food product or flavor additive of claim 1, which is a plant-based meat substitute or flavoring or a beef or pork replica or flavoring, optionally in the form of a patty, sausage or meatball.

5. A method for imparting a meat or beef like flavor to a food product, comprising formulating said food product so that it comprises 0.2% to 5% by weight of a heme-containing or porphyrin binding PX90 protein containing iron, wherein after cooking, the food product has a meat or beef like flavor or aroma.

6. The food product or flavor additive of claim 1, wherein the PX90 protein is at least 80% identical to any one of SEQ ID NOS:37, 30, 38, and 11, or a heme binding portion thereof.

7. The food product or flavor additive of claim 1, wherein the PX90 protein is an altered form of a naturally occurring heme binding protein that has enzyme activity, wherein an enzyme catalytic site has been deleted, or wherein one or more changes have been made to the protein's amino acid sequence that remove or reduce enzymatic activity of the naturally occurring protein.

8. The food product or flavor additive of claim 1, wherein the PX90 protein is at least 90% identical to SEQ. ID NO:30.

9. The food product or flavor additive of claim 1, comprising:

0.2% to 5% by weight of said heme-containing or porphyrin binding PX90 protein containing iron;

a protein content of at least 10% by weight, wherein at least 75% of the protein content is a mixture of plant proteins; and a fat content of at least 5% by weight, wherein at least 75% of the fat content is an oleogel or one or more plant derived oils.

10. The food product or flavor additive of claim 1, which is a plant-based meat substitute or replica.

* * * * *